US009801931B2

(12) United States Patent
O'Brien et al.

(10) Patent No.: US 9,801,931 B2
(45) Date of Patent: Oct. 31, 2017

(54) METHODS AND COMPOSITIONS BASED ON SHIGA TOXIN TYPE 2 PROTEIN

(71) Applicant: The Henry M. Jackson Foundation for the Advancement of Military Medicine, Inc., Bethesda, MD (US)

(72) Inventors: Alison D. O'Brien, Bethesda, MD (US); Angela Melton-Celsa, Sterling, VA (US); Michael Smith, Silver Spring, MD (US); James Sinclair, Baltimore, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 0 days.

(21) Appl. No.: 14/628,667

(22) Filed: Feb. 23, 2015

(65) Prior Publication Data

US 2016/0243210 A1    Aug. 25, 2016

Related U.S. Application Data

(62) Division of application No. 13/142,556, filed as application No. PCT/US2010/021610 on Jan. 21, 2010, now Pat. No. 8,969,529.

(60) Provisional application No. 61/210,082, filed on Mar. 13, 2009, provisional application No. 61/146,892, filed on Jan. 23, 2009.

(51) Int. Cl.
| | |
|---|---|
| *A61K 39/108* | (2006.01) |
| *A61K 39/112* | (2006.01) |
| *C07K 7/06* | (2006.01) |
| *C07K 7/08* | (2006.01) |
| *C07K 14/25* | (2006.01) |
| *C07K 16/12* | (2006.01) |
| *A61K 38/00* | (2006.01) |
| *A61K 39/00* | (2006.01) |

(52) U.S. Cl.
CPC ...... *A61K 39/0283* (2013.01); *A61K 39/0258* (2013.01); *C07K 7/06* (2013.01); *C07K 7/08* (2013.01); *C07K 14/25* (2013.01); *C07K 16/1232* (2013.01); *A61K 38/00* (2013.01); *A61K 2039/505* (2013.01); *C07K 2317/34* (2013.01)

(58) Field of Classification Search
CPC ............ C07K 2319/00; C07K 16/1225; C07K 2317/55; C07K 2317/622; C07K 2317/76; C07K 2317/94; C07K 14/245; C07K 14/25; C07K 2317/34; C07K 16/1228; C07K 16/18; C07K 2316/96; C07K 2319/55

See application file for complete search history.

(56) References Cited

U.S. PATENT DOCUMENTS

| | | | |
|---|---|---|---|
| 5,164,298 A | 11/1992 | Lingwood et al. | |
| 5,552,144 A * | 9/1996 | Samuel | C07K 14/25 424/236.1 |
| 5,747,272 A | 5/1998 | O'Brien et al. | |
| 5,866,692 A | 2/1999 | Shitara et al. | |
| 5,968,894 A | 10/1999 | Lingwood et al. | |
| 7,910,095 B2 | 3/2011 | Tzipori et al. | |
| 7,910,096 B2 | 3/2011 | Tzipori et al. | |
| 7,910,706 B2 | 3/2011 | Tzipori et al. | |
| 8,293,245 B2 | 10/2012 | Smith et al. | |
| 8,969,529 B2 | 3/2015 | O'Brien et al. | |
| 2002/0160005 A1 | 10/2002 | Tzipori et al. | |
| 2003/0082189 A1 | 5/2003 | Tzipori et al. | |
| 2003/0170248 A1 | 9/2003 | Stinson et al. | |
| 2005/0226883 A1 | 10/2005 | Averback et al. | |
| 2007/0292426 A1 | 12/2007 | Smith et al. | |
| 2008/0063598 A1 | 3/2008 | Averback et al. | |
| 2008/0107653 A1 | 5/2008 | Vermeij et al. | |
| 2009/0226469 A1 | 9/2009 | Smith et al. | |
| 2009/0258010 A1 | 10/2009 | Riviere et al. | |
| 2011/0165680 A1 | 7/2011 | Blattner et al. | |
| 2011/0318357 A1 | 12/2011 | O'Brien et al. | |
| 2012/0195891 A1 | 8/2012 | Riviere et al. | |

(Continued)

FOREIGN PATENT DOCUMENTS

| | | |
|---|---|---|
| CN | 101314616 A | 12/2008 |
| EP | 0239400 | 9/1987 |

(Continued)

OTHER PUBLICATIONS

Examiner's Report for Canadian Patent Application No. 2,748,873, dated Jan. 27, 2016 (8 pages).
Notice of Preliminary Rejection for Korean Patent Application No. 10-2011-7019455, dated Jun. 21, 2016 (15 pages) (English language translation provided).
Bitzan et al., "Safety and Pharmacokinetics of Chimeric Anti-Shiga Toxin 1 and Anti-Shiga Toxin 2 Monoclonal Antibodies in Healthy Volunteers," *Antimicrob. Agents Chemother.* 53:3081-3087 (2009).
Bose et al., "High Affinity Mouse-Human Chimeric Fab Against Hepatitis B Surface Antigen," *World J. Gastroenterol.* 11:7569-7578 (2005).
Bowie et al., "Deciphering the Message in Protein Sequences: Tolerance to Amino Acid Substitutions," *Science* 247:1306-1310 (1990).
Boyd et al., "Serological Responses to the B Subunit Shiga-Like Toxin 1 and Its Peptide Fragments Indicate that the B Subunit is a Vaccine Candidate to Counter the Action of the Toxin," *Infect. Immun.* 59(3):750-757 (1991).

(Continued)

*Primary Examiner* — Padma V Baskar
(74) *Attorney, Agent, or Firm* — Clark & Elbing LLP

(57) ABSTRACT

The invention is based on the discovery of the epitope in the Stx2 protein for the 11 E1O antibody. The invention features compositions containing non-full length Stx2 polypeptides that include the 11 E1O monoclonal antibody epitope. The invention also features methods of producing anti-Stx2 antibodies specific for the 11 E1O epitope of the Stx2 protein. Additionally, the invention features methods for treating a subject having, or at risk of developing, a Shiga toxin associated disease (e.g., hemolytic uremia syndrome and diseases associated with *E. coli* and *S. dysenteriae* infection) with a polypeptide that includes the 11 E1O epitope or with an anti-Stx2 antibody developed using the methods of the invention. Furthermore, the invention features the detection of Stx2 in a sample using the antibodies developed using the methods of the invention.

6 Claims, 15 Drawing Sheets

(56) References Cited

U.S. PATENT DOCUMENTS

| | | | |
|---|---|---|---|
| 2013/0101591 | A1 | 4/2013 | Smith et al. |
| 2014/0023652 | A1 | 1/2014 | Smith et al. |

FOREIGN PATENT DOCUMENTS

| | | |
|---|---|---|
| JP | 2003-521219 A | 7/2003 |
| WO | WO 94/04679 | 3/1994 |
| WO | WO 98/11229 | 3/1998 |
| WO | WO 98/20903 | 5/1998 |
| WO | WO 99/32645 | 7/1999 |
| WO | WO 99/45962 | 9/1999 |
| WO | WO 99/59629 | 11/1999 |
| WO | WO 2005/052158 | 6/2005 |
| WO | WO 2005/075647 | 8/2005 |
| WO | WO 2005/087794 | 9/2005 |
| WO | WO 2006/091677 | 8/2006 |
| WO | WO 2007/098201 | 8/2007 |
| WO | WO 2007/124133 | 11/2007 |
| WO | WO-2007/143004 A2 | 12/2007 |
| WO | WO 2008/080218 | 7/2008 |
| WO | WO 2009/088403 | 7/2009 |
| WO | WO 2010/085539 | 7/2010 |

OTHER PUBLICATIONS

"Investigation of an *E. coli* O157:H7 Outbreak in Brooks, Alberta, Jun.-Jul. 2002: The Role of Occult Cases in the Spread of Infection Within a Daycare Setting," *Can. Comm. Dis. Rep.* 29:21-28 (2003).

Co et al., "Humanized Antibodies for Therapy" *Nature* 351:501-502 (1991).

Cox et al., "Adjuvants—A Classification and Review of Their Modes of Action," *Vaccine* 15:248-256 (1997).

Dowling et al., "Phase 1 Safety and Pharmacokinetic Study of Chimeric Murine-Human Monoclonal Antibody cαStx2 Administered Intravenously to Healthy Adult Volunteers," *Antimicrob. Agents Chemother.* 49(5):1808-1812 (2005).

Downes et al., "Affinity Purification and Characterization of Shiga-Like Toxin II and Production of Toxin-Specific Monoclonal Antibodies," *Infect. Immun.* 56:1926-1933 (1988).

Edwards et al., "Humanization of Monoclonal Antibodies Against *Escherichia coli* Toxins STX1 and STX2," In *VTEC '97: 3rd International Symposium and Workshop on Shiga Toxin (Verocytotoxin)-Producing Escherichia coli Infections* V110/V11 p. 113 (1997) (Abstract).

Edwards et al., "Vero Cell Neutralization and Mouse Protective Efficacy of Humanized Monoclonal Antibodies Against *Escherichia coli* Toxins Stx1 and Stx2," *Escherichia coli O157:H7 and Other Shiga Toxin-Producing E. coli Strains* J. Kaper and A. O'Brien, Editors (© 1998 American Society for Microbiology, Washington, DC) 388-392 (1998).

Fagerberg et al., "Tumor Regression in Monoclonal Antibody-Treated Patients Correlates with the Presence of Anti-Idiotype-Reactive T Lymphocytes," *Cancer Res.* 55:1824-1827 (1995).

Frankel et al., "Characterization of diphtheria fusion proteins targeted to the human interleukin-3 receptor" Protein Eng. 13:575-581 (2000).

Gadermaier, E. "In shape—the art of mapping conformational epitopes" Int Arch Allergy Immunol. 157(4):321-2 (2012).

GenBank Accession No. AB083044.1, "*Escherichia coli* O157:H7 stx1 Genes for Shiga Toxin 1 Variant a Subunit, Shiga Toxin 1 Variant B Subunit, Complete CDS, Strain:Al2001/52," 2003.

Gouveia et al., "Genomic Comparisons and Shiga Toxin Production Among *Escherichia coli* O157:H7 Isolates from a Day Care Center Outbreak and Sporadic Cases in Southeastern Wisconsin," *J. Clin. Microbiol.* 36:727-733 (1998).

Greenspan et al., "Defining Epitopes: It's Not as Easy as it Seems," *Nat. Biotechnol.* 17:936-937 (1999).

Harari et al., "Carboxy-terminal Peptides from the B Subunit of Shiga Toxin Induce a Local and Parenteral Protective Effect," *Molecular Immunology* 27:613-621 (1990).

Islam et al., "Production and Characterization of Monoclonal Antibodies with Therapeutic Potential Against Shiga Toxin," *J. Clin. Lab Immunol.* 33:11-16 (1990).

Jackson et al., "Functional Analysis of the Shiga Toxin and Shiga-Like Toxin Type II Variant Binding Subunits by Using Site-Directed Mutagenesis," *J. Bacteriol.* 172:653-658 (1990).

Kelley, "Engineering Therapeutic Antibodies," *Protein Engineering: Principles and Practice* J.L. Cleland and C.S. Craik, Editors (© 1996 Wiley-Liss, Inc., Hoboken, NJ) Chapter 15:399-434 (1996).

Krautz-Peterson et al., "Intracellular neutralization of shiga toxin 2 by an a subunit-specific human monoclonal antibody," Infect Immun. 76(5):1931-1939 (2008).

LaCasse et al., "Shiga-Like Toxin-1 Receptor on Human Breast Cancer, Lymphoma, and Myeloma and Absence From $CD34^+$ Hematopoietic Stem Cells: Implications for Ex Vivo Tumor Purging and Autologous Stem Cell Transplantation," *Blood* 94(8):2901-2910 (1999).

"Lakewood-Amedex Inc. Receives Notice of Allowance on Three U.S. Patent Applications Relating to Treatment of Hemolytic Uremic Syndrome" Lakewood-Amedex Press Release dated Jan. 27, 2011.

Lindgren et al., "Virulence of Enterohemorrhagic *Escherichia coli* O91:H21 Clinical Isolates in an Orally Infected Mouse Model," *Infect. Immun.* 61:3832-3842 (1993).

LoBuglio et al., "Mouse/Human Chimeric Monoclonal Antibody in Man: Kinetics and Immune Response," *Proc. Natl. Acad. Sci. U.S.A.* 86:4220-4224 (1989).

López et al., "Shigatec Trial: A Phase II Study Assessing Monoclonal Antibodies Against Shiga Toxin 1 and 2 in Shiga Toxin-producing *E. coli*-infected Children," Poster Presentation at the $49^{th}$ IDSA Annual Meeting, Boston, USA, Oct. 20-23, 2011.

Ma et al., "Engineering an Anti-Stx2 Antibody to Control Severe Infections of EHEC O157:H7," *Immunol. Lett.* (2008) doi:10.1016/j.imlet.2008.09.008.

Marques et al., "*Escherichia coli* Strains Isolated from Pigs with Edema Disease Produce a Variant of Shiga-Like Toxin II," *FEMS Microbiol. Lett.* 44:33-38 (1987).

Melton-Celsa et al., "Protective Efficacy, Toxicity and Pharmacokinetic Evaluation in Mice of Human/Mouse Chimeric Antibodies to Stx1 and Stx2," *Abstr. Gen. Meet. Am. Soc. Microbiol.* vol. 102, 2 pages, May 19-23, 2002. (Abstract).

Miliwebsky et al., "Prolonged Fecal Shedding of Shiga Toxin-Producing *Escherichia coli* Among Children Attending Day-Care Centers in Argentina," *Revista Argentina de Microbiologia* 39:90-92 (2007).

Mills et al., "Cytotoxic necrotizing factor type 1 of uropathogenic *Escherichia coli* kills cultured human uroepithelial 5637 cells by an apoptotic mechanism," Infect Immun. 68(10):5869-5880 (2000).

Morrison, "With FDA Talks Stalled, Thallion Looks Abroad," *Bio World Today* 18(211):1-7 (2007).

O'Brien et al., "Shiga and Shiga-Like Toxins," *Microbiol. Rev.* 51:206-220 (1987).

O'Brien et al., "Immunochemical and Cytotoxic Activities of Shigella dysenteriae 1 (Shiga) and Shiga-Like Toxins," *Infect. Immun.* 35:1151-1154 (1982).

O'Donnell et al., "Outbreak of Vero Cytotoxin-Producing *Escherichia coli* O157 in a Child Day Care Facility," *Commun. Dis. Public. Health* 5:54-58 (2002) (Abstract).

Ofek et al., "Elicitation of Structure-Specific Antibodies by Epitope Scaffolds," *Proc. Natl. Acad. Sci. U.S.A.* 107: 17880-17887 (2010).

Paton et al., "Pathogenesis and Diagnosis of Shiga Toxin-Producing *Escherichia coli* Infections," *Clin. Microbiol. Rev.* 11:450-479 (1998).

Perera et al. "Isolation and Characterization of Monoclonal Antibodies to Shiga-Like Toxin II of Enterohemorrhagic *Escherichia coli* and Use of the Monoclonal Antibodies in a Colony Enzyme-Linked Immunosorbent Assay," *J. Clin. Microbiol.* 26:2127-2131 (1988).

Rüssmann et al., "Variants of Shiga-like Toxin II Constitute a Major Toxin Component in *Escherichia coli* O157 Strains From Patients With Haemolytic Uraemic Syndrome," *J. Med. Microbiol.* 40:338-343 (1994).

(56) References Cited

OTHER PUBLICATIONS

Sauter et al., "Mouse Model of Hemolytic-Uremic Syndrome Caused by Endotoxin-Free Shiga Toxin 2 (Stx2) and Protection from Lethal Outcome by Anti-Stx2 Antibody," *Infect. Immun.* 76:4469-4478 (2008).
Schmitt et al., "Two Copies of Shiga-Like Toxin II-Related Genes Common in Enterohemorrhagic *Escherichia coli* Strains Are Responsible for the Antigenic Heterogeneity of the O157:H⁻ Strain E32511," *Infect. Immun.* 59:1065-1073 (1991).
Sheoran et al., "Stx2-Specific Human Monoclonal Antibodies Protect Mice Against Lethal Infection with *Escherichia coli* Expressing Stx2 Variants," *Infect. Immun.* 71:3125-3130 (2003).
Simon et al., "Shiga Toxin 1 Elicits Diverse Biologic Responses in Mesangial Cells," *Kidney Int.* 54:1117-1127 (1998).
Singer et al., "Genes and genomes," Moscow, "Mir" vol. 1, pp. 63-64, 1998 (No English language translation provided).
Smith et al., "Epitope Mapping of Monoclonal Antibodies 13c4 and 11e10 that Neutralize Stx1 and Stx2, Respectively" presented at the 5$^{th}$ International Symposium on 'Shiga Toxin (Verocytotoxin)—Producing *Escherichia coli* Infections' Final Programme and Book of Abstracts www.VTEC2003.com Edinburgh International Conference Centre (EICC), Edinburgh, Scotland, Jun. 8-12, 2003. (Abstract).
Smith et al., "Development of a Hybrid Shiga Holotoxoid Vaccine to Elicit Heterologous Protection Against Shiga Toxins Types 1 and 2," *Vaccine* 24:4122-4129 (2006).
Smith et al., "The 13C4 Monoclonal Antibody that Neutralizes Shiga Toxin Type 1 (Stx1) Recognizes Three Regions on the Stx1 B Subunit and Prevents Stx1 From Binding to Its Eukaryotic Receptor Globotriaosylceramide," *Infect. Immun.* 74(12):6992-6998 (2006).
Smith et al., "The 13C4 Monoclonal Antibody that Neutralizes Shiga Toxin (Stx) Type 1 Binds to Three Regions on the Stx1 B Subunit," presented at the American Society for Microbiology General Meeting held in Orlando, Florida, May 21-25, 2006 (Abstract).
Smith et al., "Monoclonal Antibody 11E10, Which Neutralizes Shiga Toxin Type 2 (Stx2), Recognizes Three Regions on the Stx2 a Subunit, Blocks the Enzymatic Action of the Toxin In Vitro, and Alters the Overall Cellular Distribution of the Toxin," *Infect. Immun.* 77:2730-2740 (2009).
Speirs et al., "Detection of *Escherichia coli* Cytotoxins by Enzyme-Linked Immunosorbent Assays," *Can. J. Microbiol.* 37:650-653 (1991).
Stinson et al., "Generation of Single-Chain Antibody Fragments by PCR," *PCR Strategies*, Eds. Innis, Gelfund, and Sninsky. Boston: Academic Press, Inc., 1995. 300-312.
Strockbine et al., "Characterization of Monoclonal Antibodies Against Shiga-Like Toxin From *Escherichia coli,*" *Infect. Immun.* 50:695-700 (1985).
Strockbine et al., "Two Toxin-Converting Phages from *Escherichia coli* O157:H7 Strain 933 Encode Antigenically Distinct Toxins with Similar Biologic Activities," *Infect. Immun.* 53:135-140 (1986).
Tesh et al., "Comparison of the Relative Toxicities of Shiga-Like Toxins Type I and Type II for Mice," *Infect. Immun.* 61:3392-3402 (1993).
Turner et al., "Clinical Roundup," *BioWorld Today* 19(61):1-8 (2008).
Wen et al., "Genetic Toxoids of Shiga Toxin Types 1 and 2 Protect Mice Against Homologous But Not Heterologous Toxin Challenge," *Vaccine* 24:1142-1148 (2006).
Examiner's Report for Australian Application No. 2007240614, dated Dec. 15, 2011.
Summons to Attend Oral Proceedings Pursuant to Rule 115(1) EPC for European Application No. 07795522.7, dated Dec. 22, 2011.
EPO Communication for European Application No. 07775978.5, dated Jan. 10, 2012.
Extended European Search Report for European Application No. 07775978.5, dated Jul. 23, 2009.
Extended European Search Report for European Application No. 07795522.7, dated Feb. 25, 2010.
European Official Communication for European Application No. 98965434.8, dated Aug. 9, 2007.
Extended European Search Report for European Application No. 11179552.2, dated Jan. 20, 2012.
Notice of Reasons of Rejection for Japanese Application No. 2000-525563, dated Nov. 11, 2008. (English Translation.).
International Preliminary Report on Patentability for International Application No. PCT/US2007/009799, dated Oct. 22, 2008.
International Search Report for International Application No. PCT/US2007/009799, dated Sep. 26, 2008.
International Preliminary Report on Patentability for International Application No. PCT/US2007/012797, dated Dec. 3, 2008.
International Search Report for International Application No. PCT/US2007/012797, dated Jan. 10, 2008.
International Preliminary Report on Patentability for International Application No. PCT/US2010/021610, dated Jul. 26, 2011.
International Search Report for International Application No. PCT/US2010/021610, dated Apr. 23, 2010.
First Substantive Report for Chilean Patent Application No. 1769-2011, issued Jun. 4, 2013 (22 pages).
Second Office Action for Chinese Patent Application No. 201080005259.5, dated Nov. 4, 2013 (6 pages) (No English language translation provided).
Notification of the Second Office Action for Chinese Patent Application No. 201080005259.5, mailed Nov. 4, 2013 (10 pages).
Communication pursuant to Article 94(3) EPC for European Patent Application No. 10733840.2, dated Dec. 20, 2013.
Notice of Reasons for Rejection for Japanese Patent Application No. 2011-548095 including English language translation, dispatched Jun. 23, 2014 (8 pages).
Office Action issued by the Department for Substantive Examination in Russian Application No. 2011126896/10(039802) issued Nov. 8, 2013 (English language translation enclosed).
Second Substantive Examination Report for Chilean Patent Application No. 2011-1769, dated Jun. 4, 2014 (20 pages) (No English language translation provided).
Decision of Rejection for Japanese Patent Application No. 2011-548095 including English language translation, dispatched Mar. 4, 2015 (5 pages).
Patent Examination Report No. 1 for Australian Patent Application No. 2010206800, dated Jun. 24, 2015 (5 pages).

\* cited by examiner

Fig. 2A

```
      40-          50-
Stx1  MIDSGSGDNLFA
Stx2  V.NHTPPGSY..
          Region A 90-         100-
Stx1  YRFADFSHVTFPG
Stx2  ...S..T.ISV..
          Region B 242-                260-
Stx1  CHHHASRVARMASDEFPSMC
Stx2  ...QGA.SV.AVNE.SQPE.
             Region C
```

Fig. 2B

Fig. 7A     SEQ ID NO: 1
NHTPPGSY

Fig. 7B     SEQ ID NO: 2
THISV

Fig. 7C     SEQ ID NO: 3
QGARSVRAVNEESQPE

Fig. 7D     SEQ ID NO: 19
AHISL

Fig. 8A

SEQ ID NO: 4
```
MKIIIFRVLT FFFVIFSVNV VAKEFTLDFS TAKTYVDSLN VIRSAIGTPL  50
QTISSGGTSL LMINHTPPGS YFAVDVRGID PEEGRFNNLR LIVERNNLYV 100
TGFVNRTNNV FYRFADFSHV TFPGTTAVTL SGDSSYTTLQ RVAGISRTGM 150
QINRHSLTTS YLDLMSHSGT SLTQSVARAM LRFVTVTAEA LRFRQIQRGF 200
RTTLDDLSGR SYVMTAEDVD LTLNWGRLSS VLPDYHGQDS VRVGRISFGS 250
INAILGSVAL ILNCHHHASR VARMASDEFP SMCPADGRVR GITHNKILWD 300
SSTLGAILMR RTISS                                      315
```

Fig. 8B

SEQ ID NO: 5
```
MKIIIFRVLT FFFVIFSVNV VAKEFTLDFS TAKTYVDSLN VIRSAIGTPL  50
QTISSGGTSL LMINHTPPGS YFAVDVRGID PEEGRFNNLR LIVERNNLYV 100
TGFVNRTNNV FYRFADFTHI SVPGTTAVTL SGDSSYTTLQ RVAGISRTGM 150
QINRHSLTTS YLDLMSHSGT SLTQSVARAM LRFVTVTAEA LRFRQIQRGF 200
RTTLDDLSGR SYVMTAEDVD LTLNWGRLSS VLPDYHGQDS VRVGRISFGS 250
INAILGSVAL ILNCHHHASR VARMASDEFP SMCPADGRVR GITHNKILWD 300
SSTLGAILMR RTISS                                      315
```

Fig. 8C

SEQ ID NO: 6
```
MKIIIFRVLT FFFVIFSVNV VAKEFTLDFS TAKTYVDSLN VIRSAIGTPL  50
QTISSGGTSL LMINHTPPGS YFAVDVRGID PEEGRFNNLR LIVERNNLYV 100
TGFVNRTNNV FYRFADFSHV TFPGTTAVTL SGDSSYTTLQ RVAGISRTGM 150
QINRHSLTTS YLDLMSHSGT SLTQSVARAM LRFVTVTAEA LRFRQIQRGF 200
RTTLDDLSGR SYVMTAEDVD LTLNWGRLSS VLPDYHGQDS VRVGRISFGS 250
INAILGSVAL ILNCHHQGAR SVRAVNEESQ PECPADGRVR GITHNKILWD 300
SSTLGAILMR RTISS                                      315
```

Fig. 8D

SEQ ID NO: 7
```
MKIIIFRVLT FFFVIFSVNV VAKEFTLDFS TAKTYVDSLN VIRSAIGTPL  50
QTISSGGTSL LMIDSGSGDN LFAVDVRGID PEEGRFNNLR LIVERNNLYV 100
TGFVNRTNNV FYRFADFTHI SVPGTTAVTL SGDSSYTTLQ RVAGISRTGM 150
QINRHSLTTS YLDLMSHSGT SLTQSVARAM LRFVTVTAEA LRFRQIQRGF 200
RTTLDDLSGR SYVMTAEDVD LTLNWGRLSS VLPDYHGQDS VRVGRISFGS 250
INAILGSVAL ILNCHHQGAR SVRAVNEESQ PECPADGRVR GITHNKILWD 300
SSTLGAILMR RTISS
```

Fig. 8E

SEQ ID NO: 8
```
MKIIIFRVLT FFFVIFSVNV VAKEFTLDFS TAKTYVDSLN VIRSAIGTPL  50
QTISSGGTSL LMINHTPPGS YFAVDVRGID PEEGRFNNLR LIVERNNLYV 100
TGFVNRTNNV FYRFADFTHI SVPGTTAVTL SGDSSYTTLQ RVAGISRTGM 150
QINRHSLTTS YLDLMSHSGT SLTQSVARAM LRFVTVTAEA LRFRQIQRGF 200
RTTLDDLSGR SYVMTAEDVD LTLNWGRLSS VLPDYHGQDS VRVGRISFGS 250
INAILGSVAL ILNCHHQGAR SVRAVNEESQ PECPADGRVR GITHNKILWD 300
SSTLGAILMR RTISS                                      315
```

Fig. 9A  SEQ ID NO: 9

```
   1 ATGAAAATAA TTATTTTTAG AGTGCTAACT TTTTTCTTTG TTATCTTTTC AGTTAATGTG
  61 GTGGCGAAGG AATTTACCTT AGACTTCTCG ACTGCAAAGA CGTATGTAGA TTCCCTGAAT
 121 GTCATTCGCT CTGCAATAGG TACTCCATTA CAGACTATTT CATCAGGAGG TACGTCTTTA
 181 CTGATGATTG ATAGTGGCTC AGGGGATAAT TTGTTTGCAG TTGATGTCAG AGGGATAGAT
 241 CCAGAGGAAG GGCGGTTTAA TAATCTACGG CTTATTGTTG AACGAAATAA TTTATATGTG
 301 ACAGGATTTG TTAACAGGAC AAATAATGTT TTTTATCGCT TTGCTGATTT TTCACATGTT
 361 ACCTTTCCAG GTACAACAGC GGTTACATTG TCTGGTGACA GTAGCTATAC CACGTTACAG
 421 CGTCTTGCAG GGATCAGTCG TACGGGGATG CAGATAAATC GCCATTCGTT GACTACTTCT
 481 TATCTGGATT TAATGTCGCA TAGTGGAACC TCACTGACGC AGTCTGTGGC AAGACCGATG
 541 TTACGGTTTG TTACTGTGAC AGCTGAAGCT TTACGTTTTC GGCAAATACA GAGGGATTT
 601 CGTACAACAC TGGATGATCT CAGTGGGCGT TCTTATGTAA TGACTGCTGA AGATGTTGAT
 661 CTTACATTGA ACTGGGGAAG GTTGAGTAGC GTCCTGCCTG ACTATCATGG ACAAGACTCT
 721 GTTCGTGTAG GAAGAATTTC TTTTGGAAGC ATTAATGCAA TTCTGGGAAG CGTGGCATTA
 781 ATACTGAATT GTCATCATCA TGCATCGCGA GTTGCCAGAA TGGCATCTGA TGAGTTTCCT
 841 TCTATGTGTC CGGCAGATGG AAGAGTCCGT GGGATTACGC ACAATAAAAT ATTGTGGGAT
 901 TCATCCACTC TGGGGGCAAT TCTGATGCGC AGAACTATTA GCAGTTGAGG GGGTAAAATG
 961 AAAAAAACAT TATTAATAGC TGCATCGCTT TCATTTTTTT CAGCAAGTGC GCTGGCGACG
1021 CCTGATTGTG TAACTGGAAA GGTGGAGTAT ACAAAATATA ATGATGACGA TACCTTTACA
1081 GTTAAAGTGG GTGATAAAGA ATTATTTACC AACAGATGGA ATCTTCAGTC TCTTCTTCTC
1141 AGTGCGCAAA TTACGGGGAT GACTGTAACC ATTAAAACTA ATGCCTGTCA TAATGGAGGG
1201 GGATTCAGCG AAGTTATTTT TCGTTGA
```

Fig. 9B  SEQ ID NO: 10

```
   1 ATGAAAATAA TTATTTTTAG AGTGCTAACT TTTTTCTTTG TTATCTTTTC AGTTAATGTG
  61 GTGGCGAAGG AATTTACCTT AGACTTCTCG ACTGCAAAGA CGTATGTAGA TTCGCTGAAT
 121 GTCATTCGCT CTGCAATAGG TACTCCATTA CAGACTATTT CATCAGGAGG TACGTCTTTA
 181 CTGATGATTG ATAGTGGCTC AGGGGATAAT TTGTTTGCAG TTGATGTCAG AGGGATAGAT
 241 CCAGAGGAAG GCGGTTTAA TAATCTACGG CTTATTGTTG AACGAAATAA TTTATATGTG
 301 ACAGGATTTG TTAACAGGAC AAATAATGTT TTTTATCGCT TTGCTGATTT TTCACATGTT
 361 ACCTTTCCAG GTACAACAGC GGTTACATTG TCTGGTGACA GTAGCTATAC CACGTTACAG
 421 CGTGTTGCAG GGATCAGTCG TACGGGGATG CAGATAAATC GCCATTCGTT GACTACTTCT
 481 TATCTGGATT TAATGTCGCA TAGTGGAACC TCACTGACGC AGTCTGTGGC AACACCGATG
 541 TTACGGTTTG TTACTGTGAC AGCTGAAGCT TTACGTTTTC GGCAAATACA GAGGGATTT
 601 CGTACAACAC TGGATGATCT CAGTGGGCGT TCTTATGTAA TGACTGCTGA AGATGTTGAT
 661 CTTACATTGA ACTGGGGAAG GTTGAGTAGC GTCCTGCCTG ACTATCATGG ACAAGACTCT
 721 GTCGTGTAG GAAGAATTTC TTTTGGAAGC ATTAATGCAA TTCTGGGAAG CGTGGCATTA
 781 ATACTGAATT GTCATCATCA TGCATCGCGA GTTGCCAGAA TGGCATCTGA TGAGTTTCCT
 841 TCTATGTGTC CGGCAGATGG AAGAGTCCGT GGGATTACGC ACAATAAAAT ATTGTGGGAT
 901 TCATCCACTC TGGGGGCAAT TCTGATGCGC AGAACTATTA GCAGTTGA
```

Fig. 9C  SEQ ID NO: 11

```
   1 ATGAAAAAAA CATTATTAAT AGCTGCATCG CTTTCATTTT TTTCAGCAAG TGCGCTGGCG
  61 ACGCCTGATT GTGTAACTGG AAAGGTGGAG TATACAAAAT ATAATGATGA CGATACCTTT
 121 ACACTTAAAC TCCCTCATAA AGAATTATTT ACCAACAGAT GGAATCTTCA GTCTCTTCTT
 181 CTCAGTGCGC AAATTACGGG GATGACTGTA ACCATTAAAA CTAATGCCTG TCATAATGGA
 241 GGGGGATTCA GCGAAGTTAT TTTTCGTTGA
```

Fig. 10A   SEQ ID NO: 12

```
  1 MKIIIFRVLT FFFVIFSVNV VAKEFTLDFS TAKTYVDSLN VIRSAIGTPL QTISSGGTSL
 61 LMIDSGSGDN LFAVDVRGID PEEGRFNNLR LIVERNNLYV TGFVNRTNNV FYRFADFSHV
121 TFPGTTAVTL SGDSSYTTLQ RVAGISRTGM QINRHSLTTS YLDLMSHSGT SLTQSVARAM
181 LRFVTVTAEA LRFQIQRGF RTTLDDLSGR SYVMTAEDVD LTLNWGRLSS VLPDYHGQDS
241 VRVGRISFGS INAILGSVAL ILNCHHHASR VARMASDEFP SMCPADGRVR GITHNKILWD
301 SSTLGAILMR RTISS
```

Fig. 10B   SEQ ID NO: 13

```
  1 MKKTLLIAAS LSFFSASALA TPDCVTGKVE YTKYNDDDTF TVKVGDKELF TNRWNLQSLL
 61 LSAQITGMTV TIKTNACHNG GGFSEVIFR
```

Fig. 11A    SEQ ID NO: 14

```
   1 ATGAAGTGTA TATTATTTAA ATGGGTACTG TGCCTGTTAC TGGGTTTTTC TTCGGTATCC
  61 TATTCCCGGG AGTTTACGAT AGACTTTTCG ACCCAACAAA CTTATCTCTC TTCGTTAAAT
 121 AGTATACGGA CAGAGATATC GACCCCTCTT GAACATATAT CTCAGGGGAC CACATCGGTG
 181 TCTGTTATTA ACCACACCCC ACCGGGCAGT TATTTTGCTG TGGATATACG AGGGCTTGAT
 241 GTCTATCAGG CGCGTTTTGA CCATCTTCGT CTGATTATTG AGCAAAATAA TTTATATGTG
 301 GCCGGGTTCG TTAATACGGC AACAAATACT TTCTACCGTT TTTCAGATTT TACACATATA
 361 TCAGTGCCCG GTGTGACAAC GGTTTCCATG ACAACGGACA GCAGTTATAC CACTCTGCAA
 421 CGTGTCGCAG CGCTGGAACG TTCCGGAATG CAAATCAGTC GTCACTCACT GGTTTCATCA
 481 TATCTGGCGT TAATGGAGTT CAGTGGTAAT ACAATGACCA GAGATGCATC CAGAGCAGTT
 541 CTGCGTTTTG TCACTGTCAC AGCAGAAGCC TTACGCTTCA GGCAGATACA GAGAGAATTT
 601 CGTCAGGCAC TGTCTGAAAC TGCTCCTGTG TATACGATGA CGCCGGGAGA CGTGGACCTC
 661 ACTCTGAACT GGGGGCGAAT CAGCAATGTG CTTCCGGAGT ATCGGGGAGA GGATGGTGTC
 721 AGAGTGGGGA GAATATCCTT TAATAATATA TCAGCGATAC TGGGGACTGT CGCCCTTATA
 781 CTGAATTGCC ATCATCAGGG GGCGCGTTCT GTTCGCGCCG TGAATGAAGA GAGTCAACCA
 841 GAATGTCAGA TAACTGGCGA CAGGCCTGTT ATAAAAATAA ACAATACATT ATGGGAAAGT
 901 AATACAGCTG CAGCGTTTCT GAACAGAAAG TCACAGTTTT TATATACAAC GGGTAAATAA
 961 AGGAGTTAAG CATGAAGAAG ATGTTTATGG CGGTTTTATT TGCATTAGCT TCTGTTAATG
1021 CAATGGCGGC GGATTGTGCT AAAGGTAAAA TTGAGTTTTC CAAGTATAAT GAGGATGACA
1081 CATTTACACT GAAGGTTGAC GGGAAAGAAT ACTGGACCAG TCGCTGGAAT CTGCAACCGT
1141 TACTGCAAAG TGCTCAGTTG ACAGGAATGA CTGTCACAAT CAAATCCAGT ACCTGTGAAT
1201 CAGGCTCCGG ATTTGCTGAA GTGCAGTTTA ATAATGACTG A
```

Fig. 11B    SEQ ID NO: 15

```
   1 ATGAAGTGTA TATTATTTAA ATGGGTACTG TGCCTGTTAC TGGGTTTTTC TTCGGTATCC
  61 TATTCCCGGG AGTTTACGAT AGACTTTTCG ACCCAACAAA CTTATGTCTC TTCGTTAAAT
 121 AGTATACGGA CAGAGATATC GACCCCTCTT GAACATATAT CTCAGGGGAC CACATCGGTG
 181 TCTGTTATTA ACCACACCCC ACCGGGCAGT TATTTTGCTG TGGATATACG AGGGCTTGAT
 241 GTCTATCAGG CGCGTTTTGA CCATCTTCGT CTGATTATTG AGCAAAATAA TTTATATGTG
 301 GCCGGGTTCG TTAATACGGC AACAAATACT TTCTACCGTT TTTCAGATTT TACACATATA
 361 TCAGTGCCCG GTGTGACAAC GGTTTCCATG ACAACGGACA GCAGTTATAC CACTCTGCAA
 421 CGTGTCGCAG CGCTGGAACG TTCCGGAATC CAAATCAGTC GTCACTCACT GGTTTCATCA
 481 TATCTGGCGT TAATGGAGTT CAGTGGTAAT ACAATGACCA GAGATGCATC CAGAGCAGTT
 541 CTGCGTTTTG TCACTGTCAC AGCAGAAGCC TTACGCTTCA GGCAGATACA GAGAGAATTT
 601 CGTCAGGCAC TGTCTGAAAC TGCTCCTGTG TATACGATGA CGCCGGGAGA CGTGGACCTC
 661 ACTCTGAACT GGGGGCGAAT CAGCAATGTG CTTCCGGAGT ATCGGGGAGA GGATGGTGTC
 721 AGAGTGGGGA GAATATCCTT TAATAATATA TCAGCGATAC TGGGGACTGT GGCCGTTATA
 781 CTGAATTGCC ATCATCAGGG GGCGCGTTCT GTTCGCGCCG TGAATGAAGA GAGTCAACCA
 841 GAATGTCAGA TAACTGGCGA CAGGCCTGTT ATAAAAATAA ACAATACATT ATGGGAAAGT
 901 AATACAGCTG CAGCGTTTCT GAACAGAAAG TCACAGTTTT TATATACAAC GGGTAAATAA
```

Fig. 11C    SEQ ID NO: 16

```
   1 ATGAAGAAGA TGTTTATGGC GGTTTTATTT GCATTAGCTT CTGTTAATGC AATGGCGGCG
  61 GATTGTGCTA AAGGTAAAAT TGAGTTTTCC AAGTATAATG AGGATGACAC ATTTACAGTG
 121 AAGGTTGACG GGAAAGAATA CTGGACCAGT CGCTGGAATC TGCAACCGTT ACTGCAAAGT
 181 GCTCAGTTGA CAGGAATGAC TGTCACAATC AAATCCAGTA CCTGTGAATC AGGCTCCGGA
 241 TTTGCTGAAG TGCAGTTTAA TAATGACTGA
```

Fig. 12A  SEQ ID NO: 17

```
  1 MKCILFKWVL CLLLGFSSVS YSREFTIDFS TQQSYVSSLN SIRTEISTPL EHISQGTTSV
 61 SVINHTPPGS YFAVDIRGLD VYQARFDHLR LIIEQNNLYV AGFVNTATNT FYRFSDFTHI
121 SVPGVTTVSM TTDSSYTTLQ RVAALERSGM QISRHSLVSS YLALMEFSGN TMTRDASRAV
181 LRFVTVTAEA LRFRQIQREF RQALSETAPV YTMTPGDVDL TLNWGRISNV LPEYRGEDGV
241 RVGRISFNNI SAILGTVAVI LNCHHQGARS VRAVNEESQP ECQITGDRPV IKINNTLWES
301 NTAAAFLNRK SQFLYTTGK
```

Fig. 12B  SEQ ID NO: 18

```
  1 MKKMFMAVLF ALASVNAMAA DCAKGKIEFS KYNEDDTFTV KVDGKEYWTS RWNLQPLLQS
 61 AQLTGMTVTI KSSTCESGSG FAEVQFNND
```

METHODS AND COMPOSITIONS BASED ON SHIGA TOXIN TYPE 2 PROTEIN

STATEMENT AS TO FEDERALLY SPONSORED RESEARCH

This invention was made with government support under AI020148 awarded by the National Institutes of Health. The government has certain rights in the invention.

BACKGROUND OF THE INVENTION

In general, the invention relates to the field of treating and preventing Shiga toxin associated diseases.

In the United States, Shiga toxin (Stx)-producing *Escherichia coli* (STEC) account for about 110,000 infections per year. Enterohemorrhagic *E. coli* (EHEC), most notably the serotype O157:H7, is a subset of STEC that is noted for producing Stx mediated disease. A possible complication from an infection with a Stx-producing organism is the hemolytic uremic syndrome (HUS), which is characterized by hemolytic anemia, thrombic thrombocytopenia, and renal failure. There is approximately a 5-10% fatality rate for those with HUS and survivors may have lasting kidney damage. Currently there are no FDA approved therapies or vaccines to combat or prevent illness from a Stx-mediated disease, but several promising options for the future include: a humanized monoclonal antibody that binds to and neutralizes Stx2 and a chimeric StxA2/StxB1 toxoid that elicits a neutralizing response and provides protection against a lethal challenge of Stx1 or Stx2 or Stx1 and Stx2.

There are essentially two main types of Stxs: Stx/Stx1 and Stx2. Stx is produced from *Shigella dysenteriae* type 1, while Stx1 and Stx2 are produced from *Escherichia coli*. Stx and Stx1 are virtually identical, with only one amino acid difference in the A subunit. The mature A and B subunits of Stx1 and Stx2 have 68 and 73% similarity, respectively. Despite the amino acid sequence differences, the crystal structures of Stx and Stx2 are remarkably similar (FIG. 1). These toxins can be differentiated by polyclonal antisera: polyclonal antisera raised against Stx1 does not neutralize Stx2 and vice-versa. Variants of Stx1 and Stx2 exist and include Stx1c, Stx1d, Stx2c, Stx2d, Stx2d-activatable (Stx2-act.), Stx2e, and Stx2f.

Shiga toxins are complex holotoxins with an $AB_5$ structure. The active domain (A), contains an N-glycosidase that depurinates the 28S rRNA of the 60S ribosomal subunit, which stops protein synthesis and eventually leads to cell death. The A subunit is ~32 kDa and is proteolytically cleaved by trypsin or furin into a ~28 kDa $A_1$ subunit and a ~5 kDa $A_2$ peptide which are connected through a single disulphide bond. The $A_1$ subunit contains the active domain, and the $A_2$ peptide non-covalently tethers the active domain to the binding (B) domain. The (B) domain consists of five identical ~7.7 kDa monomers that form a pentamer through which the C-terminus of the $A_2$ peptide traverses. Each of the B subunit monomers has two cysteine residues that form a disulphide bond within each monomer. The B pentamer binds the eukaryotic receptor globotriaosyl ceramide ($Gb_3$) (or $Gb_4$ as is the case for Stx2e).

Despite the known results of exposure to these toxins, currently there is no known cure or vaccine for Stx-mediated diseases. The use of antibiotics may exacerbate the situation by increasing toxin release from bacteria. Thus, there is a need for a compound to prevent or to treat the complications of EHEC infection produced by Shiga toxin. Such a compound could be used to treat infected subjects and decrease the systemic effects of toxin on the CNS, blood, and kidneys.

In addition, if the toxin could be neutralized, antibiotics could be safely given to kill the bacteria in the GI tract. Antibiotic treatment for STEC infection are contraindicated due to the potential for the antibiotic to increase toxin production by inducing the phage that carries the toxin gene. Such a compound could also be used to prevent complications of infection by treating exposed or high risk individuals before they acquire EHEC infection. Such individuals would include children in day care or the elderly in nursing homes, where a case of EHEC diarrhea has been identified. These individuals are at increased risk of developing EHEC infection, often with severe complications, and spread of EHEC in these environments is not unusual.

SUMMARY OF THE INVENTION

Monoclonal antibody 11E10 recognizes the A subunit of Stx2 and neutralizes its cytotoxicity. Despite the 68% amino acid (aa) sequence similarity between StxA1 and StxA2, the 11E10 monoclonal antibody does not bind to StxA1. We have discovered that the 11E10 epitope encompasses a discontinuous, or conformational, epitope that spans three regions on the StxA2 monomer. The three regions of dissimilarity, which includes aa 42-49 (SEQ ID NO: 1), 96-100 (SEQ ID NO: 2) and 244-259 (SEQ ID NO: 3), are found to be located near each other on the crystal structure of the Stx2 A subunit. Therefore, we have discovered that the 11E10 epitope includes at least one, two, or all three of the sequences set forth in SEQ ID NOs: 1, 2, and 3.

Accordingly, the invention features a polypeptide that includes at least one, two, or three of the amino acid sequences set forth in SEQ ID NOs: 1, 2, and 3, where the polypeptide is not full length Stx2. The polypeptide includes at least the amino acid sequence set forth in SEQ ID NO: 1. Desirably, the polypeptide includes the amino acid sequences set forth in SEQ ID NOs: 1 and 2 or, more desirably, SEQ ID NOs: 1, 2, and 3. In one embodiment, one or more of the sequences set forth in SEQ ID NOs: 1, 2, and 3 are inserted into a non-Stx2 protein scaffold. In certain embodiments, the protein scaffold is a protein substantially identical to Stx1 or a fragment thereof, e.g., at least 90%, 91%, 92%, 93%, 94%, 95%, 96%, 97%, 98%, 99%, or 100% identical. In one embodiment, the protein scaffold is Stx1, Stx, or Stx1 bearing one or more conservative point mutations. In another embodiment, the polypeptide of the invention includes an amino acid sequence substantially identical to the amino acid sequence set forth in SEQ ID NO: 8. In yet another embodiment, the polypeptide may include fragments of Stx2 that include SEQ ID NOs: 1, 2, or 3; SEQ ID NOs: 1 and 2; or SEQ ID NOs: 1, 2, and 3, e.g., amino acids 29-297, amino acids 1-158, or amino acids 29-128 of the Stx2 polypeptide sequence, wherein the fragment is not full length Stx2. In some embodiments, the fragment is inserted into a protein scaffold, e.g., Stx or Stx1.

The invention also features a polypeptide that includes an amino acid sequence substantially identical to a fragment of the amino acid sequence set forth in SEQ ID NO: 8. In one embodiment, the fragment includes a sequence at least 80%, 85%, 90%, 91%, 92%, 93%, 94%, 95%, 96%, 97%, 98%, 99% or 100% identical to amino acids 64-122 of SEQ ID NO: 8 and further includes at least the amino acid sequence set forth in SEQ ID NO: 1. Preferably, the fragment further comprises the amino acid sequence(s) set forth in SEQ ID NO: 2 or SEQ ID NOS: 2 and 3. The fragment may be, e.g., 20, 40, 59, 60, 150, 200, 219, 236, 250, 300, or 314 amino acids in length. In certain embodiments, the polypeptide is toxoided. All of the polypeptides recited above are encompassed within the term "polypeptides of the invention."

The invention also includes nucleic acid molecules, including where the nucleic acid is linked to an expression construct in a vector and where this vector is inserted into a host cell, encoding any of the polypeptides of the invention.

In a related aspect, the invention features a composition for stimulating an immune response against Stx2 using any one of the polypeptides of the invention. Desirably, the polypeptide includes the sequences set forth in SEQ ID NOs: 1 and 2 or, more desirably, 1, 2, and 3. In any of these embodiments, the composition can further include an adjuvant. In certain embodiments, the composition does not stimulate an immune response against Stx1.

The invention also features the use of any of the polypeptides of the invention (e.g., a protein scaffold such as Stx1 into which the amino acids sequences set forth in at least one, two, or all three of SEQ ID NOs: 1, 2, or 3 are inserted). Such peptides may be useful for immunization against or treatment of any Shiga toxin associated disease including hemolytic uremia syndrome and diseases associated with *E. coli* and *S. dysenteriae* infection. In one embodiment, the peptide has at least 75%, 80%, 85%, 90%, 91%, 92%, 93%, 94%, 95%, 96%, 97%, 98%, 99%, or 100% sequence identity to the amino acid sequence set forth in SEQ ID NO: 8. In another aspect, the invention features a method of producing an anti-Stx2 antibody (e.g., monoclonal and polyclonal antibodies) or fragment thereof that specifically binds to the 11E10 epitope of Stx2. Such antibodies or fragments specifically bind to Stx2 and not to Stx1. This method includes the immunization of a mammal with a polypeptide that includes a fragment of Stx2 (i.e., not full length Stx2) that includes at least one, two, or three of the sequences set forth in SEQ ID NOs: 1, 2, and 3, where this polypeptide does not include full length Stx2. Preferably the method includes the use of a polypeptide containing at least the sequence set forth in SEQ ID NO: 1, more preferably the sequences set forth in SEQ ID NOs: 1 and 2, and even more preferably the sequences set forth in SEQ ID NOs: 1, 2, and 3. In one embodiment, the peptide includes a protein scaffold, for example a protein substantially identical to Stx1, into which one or more of the amino acid sequences set forth in SEQ ID NOs: 1, 2, and 3 are inserted. The method may include immunization of the mammal with a polypeptide containing the 11E10 epitope, for example as described herein, where the polypeptide does not include full-length Stx2. In one embodiment, a mammal is immunized with a polypeptide containing an amino acid sequence substantially identical to the amino acid sequence set forth in SEQ ID NO: 8. Anti-Stx2 antibodies produced by the above methods can be screened using standard methods known in the art or described herein including, for example, the in vitro neutralization assay, to identify antibodies that specifically bind to Stx2 and not Stx1. The immunogenic polypeptide and methods of preparing this polypeptide, along with the nucleic acid molecule that encodes this polypeptide (including where this nucleic acid is linked to an expression construct in a vector, and where this vector is inserted into a host cell), are also included as related aspects of the invention.

The invention also features anti-Stx2 antibodies or fragments thereof that specifically bind to the 11E10 epitope of Stx2, where the antibodies or fragments thereof specifically bind to Stx2 and not Stx1. Preferred antibodies of the invention bind to an epitope that includes at least one, two, or all three of the sequences set forth in SEQ ID NOs: 1, 2, and 3, desirably including at least SEQ ID NO: 1, more desirably including at least SEQ ID NOs: 1 and 2, and most desirably containing SEQ ID NOs: 1, 2, and 3. The antibody epitope can be a conformational epitope where the amino acid sequences are in proximity based on the conformation of the protein scaffold, for example, as in the chimeric proteins described herein, where one or more of the Stx2 sequences set forth in SEQ ID NOs: 1, 2, and 3 are inserted into a protein scaffold substantially identical to Stx1. The antibodies can be IgG, IgM, IgE, IgD, IgA, Fab, Fv, monoclonal and polyclonal antibodies, or antibody fragments and can be developed by the methods described herein. The antibodies preferably bind Stx2 with a $K_d$ of less than 100 nM, 50 nM, 10 nM, 1 nM, 100 pM, 10 pM, or 1 pM or less. In one example, the antibody of the invention inhibits binding of the 11E10 antibody to Stx2 or to a chimeric protein containing the 11E10 epitope, including an inhibition with a $K_d$ value of between 100 nM and 1 pM. An antibody of the invention may inhibit Stx2 binding to the eukaryotic receptor globotriaosyl ceramide (Gb3). The anti-Stx2 antibodies of the invention specifically exclude any mouse, humanized, or chimeric forms of the following antibodies 11E10, TMA-15, VTM1.1, 5C12 (including 5C12 human monoclonal antibody and r5C12), 6G3, 5H8, 11F11, 11G10, 2E1, 10E10, IG3, 2F10, 3E9, 4H9, 5A4, 5F3, 5C11, 1A4, 1A5, BC5 BB12, DC1 EH5, EA5 BA3, ED5 DF3, GB6, BA4, and cαStx2 antibodies. The invention further includes a hybridoma cell line that produces any of the antibodies of the invention.

Yet another aspect of the invention features a method of detecting Stx2 in a biological sample (e.g., tissue, cell, cell extract, bodily fluid, and biopsy sample) using any of the anti-Stx2 antibodies of the invention. Detection methods of the invention include without limitation ELISA, RIA, Western blotting, immunoprecipitation, and flow cytometry. The invention includes the diagnosis of a Shiga toxin-associated disease based on the identification of Stx2 in a sample. The invention also features an immunological test kit for detecting a Shiga toxin-associated disease, the kit including an antibody of the invention and a means for detecting an interaction between the antibody and Stx2 present in the sample.

Yet another aspect of the invention features a method of treating a Shiga toxin associated disease using an antibody as provided herein or as produced by any of the foregoing methods. Examples of Shiga toxin associated diseases include hemolytic uremia syndrome (HUS) and diseases associated with *E. coli* and *S. dysenteriae* infection. These antibodies can be administered in combination with other therapies, including, but not limited to, antibodies that specifically bind other Shiga toxin associated proteins (e.g., Stx1).

By "11E10 epitope" is meant a sequence of amino acids which, either as a result of linear structure or three dimensional conformation, forms the binding site for the 11E10 antibody. This term may include any non-full length Stx2 protein that includes sequences identical to or substantially identical to one, two, or three of the sequences set forth in SEQ ID NOs: 1, 2, and 3 (e.g., SEQ ID NOs: 1 and 2 or SEQ ID NOs: 1, 2, and 3). In desired embodiments, the 11E10 epitope includes SEQ ID NOs: 1 and 2 or 1, 2 and 3. One example of a protein that includes an 11E10 epitope is a protein that includes an amino acid sequence substantially identical to the amino acid sequence set forth in SEQ ID NO: 8.

By the terms "antibody that specifically binds to the 11E10 epitope of Stx2" or "11E10 epitope-specific antibody" is meant an antibody that binds with a $K_d$ value of between 100 nM-1 pM to a protein that includes the 11E10 epitope. Such antibodies are also characterized by little or no detectable binding to the Stx1 protein (e.g., having a $K_d$ value of greater than 100 nM, 200 nM, 500 nM, 1 µM, 10 µM, 100 µM, 1 mM or greater for Stx1). Antibody affinities may be determined using any of the assays known in the art including, but not limited to, surface plasmon resonance based assay, enzyme-linked immunoabsorbent assay (ELISA), and competition assays (e.g. RIA's). Also, the antibody may be subjected to an in vitro neutralization assay as described herein. An antibody that binds specifically to the 11E10 epitope may neutralize the cytotoxic effect of Stx2 by at least 10%, 20%, 30%, 40%, 50%, 75%, or greater, using the assays described herein or known in the art. The term specifically excludes the following mouse, chimeric, humanized or human forms of the following anti-Stx2 antibodies: 11E10, TMA-15, VTM1.1, 5C12 (including 5C12 human monoclonal antibody and r5C12 (Akiyoshi and Tzipori (2005) *Infect. Immun.* 73:4054-4061), 6G3, 5H8, 11F11, 11G10, 2E1, 10E10 (Perera et al. (1988) *J. Clin. Microbial.* 26:2127-2131), IG3, 2F10, 3E9, 4H9, 5A4, 5F3, 5C11, 1A4, 1A5 (Ma et al. (2008) *Immunol. Lett.* 121:110-115 (2008), BC5 BB12, DC1 EH5, EA5 BA3, ED5 DF3, GB6, BA4 (Downes et al. (1988) *Infect. Immun.* 56:1926-1933), cαStx2 antibodies, antibodies described in Smith et al. ((2006) *Vaccine* 24:4122-4129), antibodies described in Donohue-Rolfe et al. ((1999) *Infect Immun.* 67:3645-364), and antibodies described in Sheoran et al. ((2003) *Infect Immun.* 71:3125-3130).

By "inhibit binding" is meant to cause a decrease in one protein binding to another protein by at least 50%, preferably 60%, 70%, 80%, 90%, or more, as measured, for example, by Western blot as described herein or by ELISA or the $Gb_3$ receptor binding assays known in the art.

The term "antibody" is used in the broadest sense and includes monoclonal antibodies (including full length monoclonal antibodies), polyclonal antibodies, multispecific antibodies (e.g., bispecific antibodies), or antibody fragments, provided such molecules possess a desired biological activity (e.g., neutralization of the Stx2 toxin as described herein).

As used herein, "purified" or "isolated" refers to a protein that has been identified and separated and/or recovered from a component of its natural environment. Contaminant components of its natural environment are materials that would typically interfere with diagnostic or therapeutic uses for the protein, and may include enzymes, hormones, and other proteinaceous or non-proteinaceous solutes.

By "toxoided" is meant altered, for example, by mutation, conjugation, or cross-linking, in a manner to diminish cytotoxicity while maintaining antigenicity. Toxoided versions of Stx2 include formaldehyde- and gluteraldehyde-treated Stx2 and Stx2 with a Y77S mutation. Other non-limiting examples of toxoided Stx proteins are Stx2 bearing Y77S and E167Q mutations (Wen et al. (2006) *Vaccine* 24: 1142-1148), Stx2 bearing a E167D and 6 histidine tag (Robinson et al. (2006) *Proc. Natl. Acad. Sci. U.S.A* 103:9667-9672), StxA2/StxB1 toxoid bearing Y77S, E167Q, and R170L mutations (Smith et al, *Vaccine* 24:4122-4129 (2006)). Other examples are described in Gordon et al. ((1992) *Infect. Immunol.* 60(2):485-490).

By "non-full length Stx2" is meant a protein that contains fewer than 90%, 85%, 80%, 75%, 70%, 65%, 60%, or fewer amino acids of the full length Stx2 polypeptide. Examples of non-full length Stx2 include but are not limited to the amino acid sequences set forth in SEQ ID NOs: 4-8. Other examples include polypeptides that include or consist of amino acids 29-297, 1-158, or 29-128 of Stx2, including, for example the chimeric polypeptides provided in FIG. 1A. The A subunit for wild-type Stx1, Stx2 or the chimeric toxins described within this application all have a 22 amino acid leader sequence that is removed, thus generating the mature A subunit protein.

For the purposes of this specification, the term "full-length Stx2" and the amino acid numbering of Stx2 fragments refer to the full-length mature StxA2 subunit. This mature A subunit is later asymmetrically cleaved by trypsin or furin into an A1 fragment (N-terminal ~248 amino acids) and a A2 peptide (C-terminal ~50 aa's). The A subunit, either native or chimeric in form, is usually present in the context of the holotoxin; however, expressed alone (e.g., without the B subunit), an A subunit or fragment thereof could elicit an immune response against the 11E10 epitope.

As used herein, the term "protein scaffold" or "scaffold" refers to a protein structure that has inserted into it one or more amino acid sequences of a heterologous protein, e.g., an Stx2 amino acid sequence set forth in SEQ ID NOs: 1, 2, or 3. Preferably, the three-dimensional structure of a protein scaffold is known, and the fragments of the heterologous protein are inserted at strategic locations, e.g., at surface-exposed loops or at regions of structural homology between the protein scaffold and the heterologous protein. The insertion of a fragment of Stx2 may be accompanied by selective deletion of certain sequences of the protein scaffold, e.g., a sequence having structural homology to the sequence that will be inserted. In this instance, the non-deleted sequences of the protein scaffold may be used for determining percent sequence identity to another protein, e.g., Stx1. Exemplary proteins that have been used as protein scaffolds are Stx or Stx1 (described herein), green fluorescent protein (Abedi et al. (1998) *Nucleic Acids Res.* 26:623-630), and cytotoxic T-lymphocyte-associated antigen 4 (CTLA-4) (Hufton et al. (2000) *FEBS lett.* 475:225-231). Protein scaffolds specifically exclude a protein tag, e.g., FLAG epitope or glutathione-S-transferase, to the end of which a heterologous protein sequence is fused.

By "substantially identical" is meant a nucleic acid or amino acid sequence that, when optimally aligned, for example using the methods described below, share at least 75%, 80%, 85%, 90%, 91%, 92%, 93%, 94%, 95%, 96%, 97%, 98%, 99%, or 100% sequence identity with a second nucleic acid or amino acid sequence, e.g., a Stx2, Stx1, or a chimeric protein such as the one set forth in SEQ ID NO: 8. "Substantial identity" may be used to refer to various types and lengths of sequence, such as full-length sequence, epitopes or immunogenic peptides, functional domains, coding and/or regulatory sequences, exons, introns, promoters, and genomic sequences. Percent identity between two polypeptides or nucleic acid sequences is determined in various ways that are within the skill in the art, for instance, using publicly available computer software such as Smith Waterman Alignment (Smith, T. F. and M. S. Waterman (1981) *J. Mol. Biol.* 147:195-7); "Best Fit" (Smith and Waterman (1981) Advances in Applied Mathematics, 482-489) as incorporated into GeneMatcher Plus™ (Schwarz and Dayhof (1979) Atlas of Protein Sequence and Structure, Dayhoff, M. O., Ed pp 353-358); BLAST program (Basic Local Alignment Search Tool (Altschul, S. F., W. Gish, et al. (1990) *J. Mol. Biol.* 215: 403-10), BLAST-2, BLAST-P, BLAST-N, BLAST-X, WU-BLAST-2, ALIGN, ALIGN-2, CLUSTAL, or Megalign (DNASTAR) software. In addition, those skilled in the art can determine appropriate parameters for measuring alignment, including any algorithms needed to achieve maximal alignment over the length of the sequences being compared. In general, for proteins, the length of comparison sequences can be at least 5 amino acids, preferably 10, 25, 50, 100, 150, 200, 300, or 315 amino acids or more up to the entire length of the protein. For nucleic acids, the length of comparison sequences can generally be at least 15, 75, 150, 300, 450, 600, 900, or 945 nucleotides or more up to the entire length of the nucleic acid molecule. It is understood that for the purposes of determining sequence identity when comparing a DNA sequence to an RNA sequence, a thymine nucleotide is equivalent to a uracil nucleotide. In one embodiment, the sequence identity of a protein, for example, the mature A subunit of a Shiga toxin protein, can be measured over the length of a fragment of SEQ ID NO: 8, e.g., from amino acids 64 to 122 or 64 to 282 of SEQ ID NO: 8. For amino acid sequences, conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By "fragment" is meant a portion of a polypeptide or nucleic acid molecule that contains less than 100% of the entire length of the reference nucleic acid molecule or polypeptide, preferably, at least 2%, 5%, 10%, 20%, 30%, 40%, 50%, 60%, 70%, 80%, 90%, 95%. A fragment may contain, e.g., 10, 15, 75, 150, 300, 450, 600, 900, or 945 or more nucleotides or 4, 5, 10, 25, 50, 100, 150, 200, 300, 315 amino acids or more. Fragments of Shiga toxin type 1 or Shiga toxin type 2 protein can include any portion that is less than the full-length protein, for example, a fragment of 4, 5, 8, 10, 25, 50, 100, 150, 200, 300, 315, or more amino acids in length. In one example, a fragment includes amino acids 64 to 122 or 64 to 282 of SEQ ID NO: 8.

By "Shiga toxin associated disease" is meant any disease resulting from a pathogen expressing a Shiga toxin. The term "Shiga toxin associated disease" is meant to include hemolytic uremia syndrome, shigellosis, and diseases resulting from Shiga toxin-producing *Escherichia coli* and *S. dysenteriae* infection.

BRIEF DESCRIPTION OF DRAWINGS

FIG. 2A shows amino acid alignment of StxA1 and StxA2 in the three regions that comprise the 11E10 monoclonal antibody epitope. The black and gray amino acids depict conserved and non-conserved amino acids, respectively; the dots represent identical residues. The three regions of the 11E10 monoclonal antibody epitope are as follows: region A (StxA2 residues 42-49), region B (StxA2 residues 96-100); region C (StxA2 residues 244-259). The numbering of the amino acids shown in the alignments is in respect to the StxA1 mature protein. StxA1 has an extra amino acid at position 185; this addition causes region C the epitope in StxA2 to be one number different than the corresponding region of Stx1.

FIG. 2B shows a ribbon diagram of the Stx2 crystal structure that shows the Stx2 A$_1$ and B subunits in light grey, except for three regions of the 11E10 monoclonal antibody epitope. Regions A (green), B (blue), and C (cyan) are labeled with black, gray, and white arrows, respectively. The A$_2$ peptide is depicted in black, and the active site (red) is marked with an asterisk.

Figure 1A:
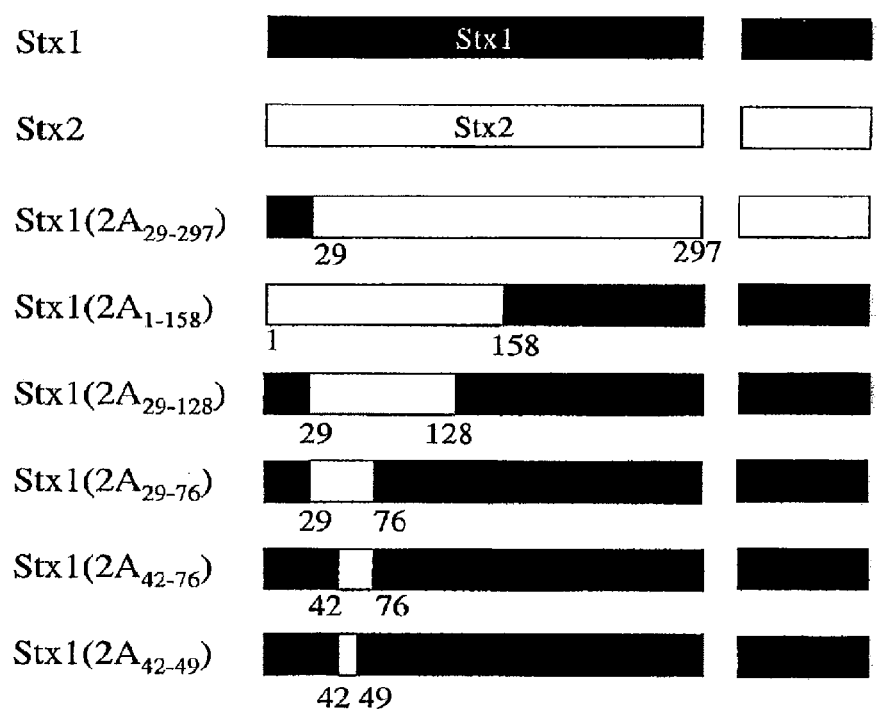
FIG. 1A illustrates initial hybrid Stx1/Stx2 A subunits. Stx1 is presented in black, Stx2 is depicted in white. The names of the chimeric toxins are shown to the left of the respective chimeric proteins, and the regions of Stx2 are listed beneath the chimeric A subunits.

After hybridoma cells are identified that produce antibodies of the desired specificity, affinity, and/or activity, the clones may be subcloned by limiting dilution procedures and grown by standard methods (Goding, supra). In addition, the hybridoma cells may be grown in vivo as ascites tumors in an animal. The monoclonal antibodies secreted by the subclones are suitably separated from the culture medium, ascites fluid, or serum by conventional immunoglobulin purification procedures such as, for example, protein A-Sepharose, hydroxyapatite chromatography, gel electrophoresis, dialysis, or affinity chromatography.

DNA encoding the monoclonal antibodies of the invention is readily isolated and sequenced using conventional procedures (e.g., using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as *E. coli* cells, COS cells, Chinese hamster ovary (CHO) cells, or myeloma cells that do not otherwise produce immunoglobulin protein, to obtain the synthesis of monoclonal antibodies in the recombinant host cells (see e.g., Skerra et al. (1993) *Curr Opin Immunol.* 5: 256-262 and Pluckthun (1992) *Immunol Rev.* 130: 151-188).

The DNA also may be modified, for example, by substituting all or part of the coding sequence for human heavy- and light-chain constant domains in place of the homologous murine sequences (Morrison et al. (1984) *Proc Natl Acad Sci. U.S.A.* 81: 6851-6855), or by covalently joining to the immunoglobulin coding sequence all or part of the coding sequence for a non-immunoglobulin polypeptide. In that manner, chimeric or hybrid antibodies are prepared that have the binding specificity of an anti-11E10 epitope monoclonal antibody. Typically such non-immunoglobulin polypeptides are substituted for the constant domains of an antibody of the invention, or they are substituted for the variable domains of one antigen-combining site of an antibody of the invention to create a chimeric bivalent antibody including one antigen-combining site having specificity for the 11E10 epitope according to the invention and another antigen-combining site having specificity for a different antigen.

Modified Antibodies

Modified antibodies of the invention include, but are not limited to, chimeric monoclonal antibodies (for example, human-mouse chimeras), human monoclonal antibodies, and humanized monoclonal antibodies. A chimeric antibody is a molecule in which different portions are derived from different animal species, such as those having a human immunoglobulin constant region and a variable region derived from a murine mAb (see, e.g., U.S. Pat. Nos. 4,816,567 and 4,816,397). Humanized forms of non-human (e.g., murine) antibodies are chimeric immunoglobulins, immunoglobulin chains, or fragments thereof (such as Fv, Fab, Fab', F(ab')$_2$ or other antigen-binding subsequences of antibodies) which contain minimal sequence derived from non-human immunoglobulin, such as one or more complementarity determining regions (CDRs) from the non-human species and a framework region from a human immunoglobulin molecule (see, e.g., U.S. Pat. No. 5,585,089).

Humanized antibodies include human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework residues of the human immunoglobulin are replaced by corresponding non-human residues. Humanized antibodies may also include residues which are found neither in the recipient antibody nor in the imported CDR or framework sequences. In general, the humanized antibody will include substantially all of at least one, and typically two, variable domains, in which all or substantially all of the CDR regions correspond to those of a non-human immunoglobulin, and all or substantially all of the FR regions are those of a human immunoglobulin consensus sequence. The humanized antibody optimally also will include at least a portion of an immunoglobulin constant region (Fc), typically that of a human immunoglobulin.

Chimeric and humanized monoclonal antibodies can be produced by recombinant DNA techniques known in the art, for example using methods described in WO 87/02671; EP 184,187; EP 171,496; EP 173,494; WO 86/01533; U.S. Pat. No. 4,816,567; EP 125,023; Better et al. (1988) *Science* 240: 1041-1043; Liu et al. ((1987) *Proc Natl Acad Sci. U.S.A.* 84: 3439-3443); Liu et al. ((1987) *J Immunol.* 139: 3521-3526); Sun et al. ((1987) *Proc Natl Acad Sci. U.S.A.* 84: 214-218); Nishimura et al. ((1987) *Cancer Res.* 47: 999-1005); Wood et al. ((1985) *Nature* 314: 446-449); Shaw et al. ((1988) *J Natl Cancer Inst.* 80: 1553-1559); Morrison ((1985) *Science* 229: 1202-1207); Oi et al. ((1986) *Biotechniques.* 4: 214); U.S. Pat. No. 5,225,539; Jones et al. ((1986) *Nature* 321: 552-525); Verhoeyan et al. ((1988) *Science* 239: 1534); and Beidler et al. ((1988) *J Immunol.* 141: 4053-4060). See below for a further discussion of humanized antibodies and methods related thereto.

Another highly efficient means for generating recombinant antibodies is disclosed by Newman ((1992) *Biotechnology.* 10: 1455-1460). See also U.S. Pat. Nos. 5,756,096; 5,750,105; 5,693,780; 5,681,722; and 5,658,570.

Methods for humanizing non-human antibodies are well known in the art. Humanization may be essentially performed following the method of Winter and co-workers as described above (including Jones et al. ((1986) *Nature* 321: 522-525); Riechmann et al. ((1988) *Nature* 332: 323-327); Verhoeyen et al. ((1988) *Science* 239: 1534-1536), by substituting rodent CDRs or CDR sequences for the corresponding sequences of a human antibody. Accordingly, such humanized antibodies are chimeric antibodies (see U.S. Pat. Nos. 4,816,567 and 6,331,415). In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called best-fit method, the sequence of the variable domain of a rodent antibody is screened against the entire library of known human variable-domain sequences. The human sequence which is closest to that of the rodent is then accepted as the human framework (FR) for the humanized antibody (Sims et al. (1993) *J Immunol.* 151: 2296-2308; Chothia and Lesk (1987) *J Mol Biol.* 196: 901-917). Another method uses a particular framework derived from the consensus sequence of all human antibodies of a particular subgroup of light or heavy chains. The same framework may be used for several different humanized antibodies (Carter et al. (1992) *Proc Natl Acad Sci. U.S.A.* 89: 4285-4289; Presta et al. (1993) *J Immunol.* 151: 2623-2632).

It is also desired that antibodies be humanized with retention of high affinity for the antigen (i.e., the 11E10 epitope of Stx2) and other favorable biological properties. To achieve this goal, humanized antibodies are prepared through an analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues may be selected and combined from the consensus and import sequences so that the desired antibody characteristic, such as increased affinity for the target antigen(s), is achieved. In general, the CDR residues are directly and most substantially involved in influencing antigen binding.

Completely human antibodies are useful for therapeutic treatment of human subjects. Such antibodies may be produced, for example, using transgenic mice which are incapable of expressing endogenous immunoglobulin heavy and light chain genes, but which can express human heavy and light chain genes. The transgenic mice may be immunized in the normal fashion with a selected antigen, e.g., a polypeptide that includes the 11E10 epitope. For examples, see PCT Publication Nos. WO 94/02602, WO 00/76310; U.S. Pat. Nos. 5,545,806; 5,545,807; 5,569,825; 6,150,584; 6,512,097; and 6,657,103; Jakobovits et al. ((1993) *Proc Natl Acad Sci. U.S.A.* 90: 2551); Jakobovits et al. ((1993) *Nature* 362: 255-258); Bruggemann et al. ((1993) *Year in Immunol.* 7: 33-40); Mendez et al. ((1997) *Nat Gene.* 15: 146-156), and Green and Jakobovits ((1998) *J Exp Med.* 188: 483-495).

Human monoclonal antibodies can also be made by the hybridoma method. Human myeloma and mouse-human heteromyeloma cell lines for the production of human monoclonal antibodies have been described, for example, by Kozbor ((1984) *J Immunol.* 133: 3001-3005); Brodeur et al. ((1987) Monoclonal Antibody Production Techniques and Applications, pp. 51-63, Marcel Dekker, Inc., New York); and Boerner et al. ((1991) *J Immunol.* 147: 86-95).

Completely human antibodies which recognize a selected epitope can also be generated using a technique referred to as guided selection. In this approach, a selected non-human monoclonal antibody, e.g. a mouse antibody, is used to guide the selection of a completely human antibody recognizing the same epitope (Jespers et al. (1994) *Biotechnology.* 12: 899-903).

Examples of techniques which can be used to produce single-chain Fvs and antibodies include those described in U.S. Pat. Nos. 4,946,778 and 5,258,498; Huston et al. ((1991) *Meth Enzymol.* 203: 46-88); Shu et al. ((1993) *Proc Natl Acad Sci. U.S.A.* 90: 7995-7999); and Skerra et al. ((1988) *Science* 240: 1038-1040).

Alternatively, phage display technology (McCafferty et al. (1990) *Nature* 348: 552-553) can be used to produce human antibodies and antibody fragments in vitro, from immunoglobulin variable (V) domain gene repertoires from non-immunized donors. Phage display can be performed in a variety of formats. See, for example, Johnson and Chiswell ((1993) *Curr Opin Struct Biol.* 3: 564-571). Several sources of V-gene segments can be used for phage display. Clackson et al. ((1991) *Nature* 352: 624-628) isolated a diverse array of anti-oxazolone antibodies from a small random combinatorial library of V genes derived from the spleens of immunized mice. A repertoire of V genes from non-immunized human donors can be constructed and antibodies to a diverse array of antigens (including self-antigens) can be isolated essentially following the techniques described by Marks et al. ((1991) *J Mol Biol.* 222: 581-597), or Griffith et al. ((1993) *EMBO J.* 12: 725-734).

The invention provides functionally-active fragments, derivatives or analogues of the immunoglobulin molecules which specifically bind to a protein that includes the 11E10 epitope. Functionally-active in this context means that the fragment, derivative, or analogue is able to induce anti-anti-idiotype antibodies (i.e. tertiary antibodies) that recognize the same antigen that is recognized by the antibody from which the fragment, derivative or analogue is derived. Specifically, in a preferred embodiment, the antigenicity of the idiotype of the immunoglobulin molecule may be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art.

The present invention provides antibody fragments such as, but not limited to, $F(ab')_2$, $F(ab)_2$, Fab', Fab, and scFvs. Antibody fragments which recognize specific epitopes may be generated by known techniques, e.g., by pepsin or papain-mediated cleavage.

The invention also provides heavy chain and light chain dimers of the antibodies of the invention, or any minimal fragment thereof such as Fvs or single chain antibodies (SCAs) (e.g., as described in U.S. Pat. No. 4,946,778; Bird ((1988) *Science* 242: 423-42); Huston et al. ((1988) *Proc Natl Acad Sci. U.S.A.* 85: 5879-5883); and Ward et al. ((1989) *Nature* 334: 544-54), or any other molecule with the same specificity as the antibody of the invention. Single chain antibodies are formed by linking the heavy and light chain fragments of the Fv region via an amino acid bridge, resulting in a single chain polypeptide. Techniques for the assembly of functional Fv fragments in *E. coli* may be used (Skerra et al. (1988) *Science* 242: 1038-1041).

Alternatively, a clone encoding at least the Fab portion of the antibody may be obtained by screening Fab expression libraries (e.g., as described in Huse et al. ((1989) *Science* 246: 1275-1281)) for clones of Fab fragments that bind the specific antigen or by screening antibody libraries (see, e.g., Clackson et al. ((1991) *Nature* 352: 624-628) and Hanes and Pluckthun ((1997) *Proc Natl Acad Sci. U.S.A.* 94: 4937-4942)).

In other embodiments, the invention provides fusion proteins of the immunoglobulins of the invention, or functionally active fragments thereof. In one example, the immunoglobulin is fused via a covalent bond (e.g., a peptide bond), at either the N-terminus or the C-terminus to an amino acid sequence of another protein (or portion thereof, preferably at least an 10, 20 or 50 amino acid portion of the protein) that is not the immunoglobulin. Preferably the immunoglobulin, or fragment thereof, is covalently linked to the other protein at the N-terminus of the constant domain. As stated above, such fusion proteins may facilitate purification, increase half-life in vivo, and enhance the delivery of an antigen across an epithelial barrier to the immune system.

In another embodiment, the invention provides for the compositions and use of pooled antibodies, antibody fragments, and the other antibody variants described herein. For example, two or more monoclonals may be pooled for use.

In one particular embodiment, an antibody of the invention is pooled with an antibody that specifically binds to Stx or Stx1.

Therapeutic Administration

The invention also features the administration of antibodies developed using the methods above (e.g., antibodies which specifically bind the 11E10 epitope of Stx2) to subjects having, or at risk of developing a Shiga toxin associated disease.

The antibodies of the invention will be formulated, dosed, and administered in a fashion consistent with good medical practice. Factors for consideration in this context include the particular disorder being treated, the particular subject being treated, the clinical condition of the individual subject, the cause of the disorder, the site of delivery of the agent, the method of administration, the scheduling of administration, and other factors known to medical practitioners. The therapeutically effective amount of antibody that specifically binds to the 11E10 epitope of Stx2 to be administered will be governed by such considerations, and is the minimum amount necessary to prevent, ameliorate, treat, or stabilize, a Shiga toxin associated disease, or symptoms associated therewith. The antibody specific for the 11E10 epitope need not be, but is optionally formulated with one or more agents currently used to prevent or treat Shiga toxin associated diseases (e.g., antibodies specific for Stx1, including 13C4, or humanized or chimeric derivatives thereof). The effective amount of such other agents depends on the amount of antibody specific for the 11E10 epitope of Stx2 present in the formulation, the type of disorder or treatment, and other factors discussed above.

The antibody is administered by any suitable means, including parenteral, subcutaneous, intraperitoneal, intrapulmonary, and intranasal. Parenteral infusions include intramuscular, intravenous, intraarterial, intraperitoneal, or subcutaneous administration. In addition, the antibody is suitably administered by pulse infusion, particularly with declining doses of the antibody. Preferably the dosing is given by injections, most preferably intravenous or subcutaneous injections, depending in part on whether the administration is brief or chronic.

III. Vaccines

The invention features compositions for stimulating an immune response against the Stx2 protein.

Individuals having or at risk of developing a Shiga toxin associated disease can be treated by administration of a composition (e.g., a vaccine) containing the 11E10 epitope of the invention, where the polypeptide does not include full-length Stx2 polypeptide or the processed StxA2 subunit, preferably in an immunogenically effective amount. The composition can be administered prophylacticly and/or therapeutically.

Different types of vaccines can be developed according to standard procedures known in the art. For example, a vaccine may be a peptide-based (see, for example, Smith et al. ((2006) *Vaccine* 24:4122-4129)), nucleic acid-based (e.g., see Bentacor et al., "DNA vaccine encoding the enterohemorragic *Escherichia coli* 1 (EHEC) Shiga-like toxin 2 (Stx2) A2 and B subunits confers protective immunity to Stx challenge in the murine model" *Clin. Vaccine Immunol.* (e-publication ahead of print, PMID 19176691)), bacterial- or viral-based vaccines. A vaccine formulation containing a polypeptide or nucleic acid that encodes the polypeptide that includes the 11E10 epitope may contain a variety of other components, including stabilizers. The vaccine can also include or be co-administered with, one or more suitable adjuvants. The ratio of adjuvant to the polypeptide that includes the 11E10 epitope in the vaccine may be determined by standard methods by one skilled in the art.

In another embodiment, peptide vaccines may utilize peptides including the 11E10 epitope or functional derivatives thereof as a prophylactic or therapeutic vaccine in a number of ways, including: 1) as monomers or multimers of the same sequence, 2) combined contiguously or non-contiguously with additional sequences that may facilitate aggregation, promote presentation or processing of the epitope (e.g., class I/II targeting sequences) and/or an additional antibody, T helper or CTL epitopes to increase the immunogenicity of the 11E10 epitope, 3) chemically modified or conjugated to agents that would increase the immunogenicity or delivery of the vaccine (e.g., fatty acid or acyl chains, KLH, tetanus toxoid, or cholera toxin), 4) any combination of the above, 5) any of the above in combination with adjuvants, including but not limited to inorganic gels such as aluminium hydroxide, and water-in-oil emulsions such as incomplete Freund's adjuvant, aluminum salts, saponins or triterpenes, MPL, cholera toxin, ISCOM'S®, PROVAX®, DETOX®, SAF, Freund's adjuvant, Alum®, Saponin®, among others, and particularly those described in U.S. Pat. Nos. 5,709,860; 5,695,770; and 5,585,103; and/or in combination with delivery vehicles, including but not limited to liposomes, VPLs or virus-like particles, microemulsions, attenuated or killed bacterial and viral vectors, and degradable microspheres (see e.g., Kersten and Hirschberg ((2004) *Expert Rev of Vaccines.* 3: 453 462); Sheikh et al. ((2000) *Curr Opin Mol Ther.* 2: 37-54)), and 6) administered by any route or as a means to load cells with antigen ex vivo.

Dosages of a polypeptide that includes an 11E10 epitope, where the polypeptide is not full length Stx2, administered to the individual as either a prophylactic therapy or therapy against a Shiga toxin associated disease can be determined by one skilled in the art. Generally, dosages will contain between about 10 µg to 1,000 mg, preferably between about 10 mg and 500 mg, more preferably between about 30 mg and 120 mg, more preferably between about 40 mg and 70 mg, most preferably about 60 mg of the polypeptide that includes the 11E10 epitope.

At least one dose of the polypeptide that includes the 11E10 epitope will be administered to the subject, preferably at least two doses, more preferably four doses, with up to six or more total doses administered. It may be desirable to administer booster doses of the polypeptide that includes the 11E10 epitope at one or two week intervals after the last immunization, generally one booster dose containing less than or the same amount of the 11E10 epitope as the initial dose administered. In one example, the immunization regimen will be administered in four doses at one week intervals. Since a polypeptide or a nucleic acid may be broken down in the stomach, the immunization is preferably administered parenterally (e.g., subcutaneous, intramuscular, intravenous, or intradermal injection). The progress of immunized subjects may be followed by general medical evaluation, screening for infection by serology and/or gastroscopic examination.

IV. Examples

EXAMPLE 1

Monoclonal antibody 11E10 recognizes the $A_1$ subunit of Stx2. The binding of 11E10 to Stx2 neutralizes both the cytotoxic and lethal activities of Stx2, but the monoclonal antibody does not bind to or neutralize Stx1 despite the 55% identity and 68% similarity in the amino acids of the mature A subunits. In this study, we sought to identify the segment(s) on Stx2 that constitutes the 11E10 epitope and to determine how recognition of that region by 11E10 leads to inactivation of the toxin. Toward those objectives, we generated a set of chimeric Stx1/Stx2 molecules and then evaluated the capacity of 11E10 to recognize those hybrid toxins by Western blot analyses and to neutralize them in Vero cell cytotoxicity assays. We also compared the amino acid sequences and crystal structures of Stx1 and Stx2 for stretches of dissimilarity that might predict a binding epitope on Stx2 for 11E10. Through these assessments, we concluded that the 11E10 epitope is comprised of three non-contiguous regions surrounding the Stx2 active site. To ask how 11E10 neutralizes Stx2, we examined the capacity of 11E10/Stx2 complexes to target ribosomes. We found that the binding of 11E10 to Stx2 prevented the toxin from inhibiting protein synthesis in an in vitro assay but also altered the overall cellular distribution of Stx2 in Vero cells. We propose that the binding of the 11E10 monoclonal antibody to Stx2 neutralizes at least some if not all of the effects of the toxin and may do so by preventing the toxin from reaching or inactivating the ribosomes.

We have investigated passive immunization strategies to neutralize the Stxs associated with STEC infections (Dowling et al. (2005) *Antimicrob. AgentsChemother.* 49:1808-1812, Edwards et al. (1998) In J. B. Kaper and A. D. O'Brien (ed.), *Escherichia coli* O157:H7 and other Shiga toxin-producing *E. coli* strains. ASM Press, Washington, D.C., Kimura et al. (2002) *Hybrid. Hybridomics.* 21:161-168, Ma et al. (2008) *Immunol. Lett.* 121:110-115, Mukherjee et al. (2002) *Infect. Immun.* 70:612-619, Mukherjee et al. (2002) *Infect. Immun.* 70:5896-5899.). Our passive immunization strategy is based on murine monoclonal antibodies developed in this laboratory that specifically bind to and neutralize Stx/Stx1 or Stx2 (Strockbine et al. (1985) *Infect. Immun.* 50:695-700, Perera et al. (1988) *J Clin. Microbiol.* 26:2127-2131). The monoclonal antibody 11E10 was generated by immunization of BALB/c mice with Stx2 toxoided by treatment with formaldehyde (Perera et al., supra). By Western blot analysis, the 11E10 monoclonal antibody specifically recognizes the $A_1$ fragment of Stx2 and neutralizes Stx2 for Vero cells and mice but does not bind to or neutralize Stx/Stx1 (Edwards et al., supra; Perera et al. supra. The murine 11E10 monoclonal antibody was modified to contain a human constant region to reduce the potential for an antibody recipient to generate an anti-mouse antibody response. This human/mouse chimeric antibody, called cαStx2, successfully underwent Phase I clinical testing (Dowling et al., supra). In this report, we define the epitope on the A subunit of Stx2 recognized by the murine 11E10 monoclonal antibody (and, therefore, also by cαStx2) on the A subunit of Stx2, and present evidence that the monoclonal antibody blocks the enzymatic action of the toxin in vitro and also alters toxin trafficking in Vero cells.

Materials and Methods

Bacterial strains, plasmids, purified Stx1 and Stx2, and monoclonal antibodies 11E10 and 13C4.

Bacteria were grown in Luria-Bertani (LB) broth or on LB agar (Becton Dickinson and Company, Sparks, Md.) supplemented with 100 µg/ml of ampicillin as needed for selection of recombinant plasmids. Bacterial strains and plasmids used in this study are listed in Table 1. Stx1 and Stx2 were purified by affinity chromatography as described previously (Melton-Celsa and O'Brien (2000) p. 385-406. In Handbook of Experimental Pharmacology, vol. 145. Springer-Verlag, Berlin) and the monoclonal antibodies 11E10, 11F11 (specific for Stx2 (Perera et al., supra), and 13C4 (specific for Stx1 (Strockbine et al. (1985) [*Infect. Immun.* 50:695-700)] were produced in this laboratory and deposited with BEI Resources (Manassas, Va.).

TABLE 1

Bacterial strains and plasmids used in this study.

| Strain or plasmid | Relevant characteristics | Source or reference |
|---|---|---|
| *E. coli* strains | | |
| Dh5α | F-_80 dlacZ_M15_(lacZYA-argF)U169 endA1 recA1hsdR17(rK-mK+) deoR thi-1 phoA supE44_-gyrA96 relA1 | Gibco BRL |
| XL10 Gold | Tetr Δ(mcrA)183 Δ(mcrCB-hsdSMR-mrr)173 endA1 supE44 thi-1 recA1 gyrA96 relA1 lac Htc [F' proAB lacIqZΔM15 Tn10 (Tetr) Amy Camr] | Stratagene |
| Bl21 (DE3) | FompT hsd$S_B$ ($r_B$-$m_b$-) gal dcm (DE3) | Novagen |
| EH250 | *E. coli* Ount:H12 isolate; Stx2d producer | Pierard et al. (1998) J Clin Microbiol 36: 3317-3322 |
| Cloning Vectors | | |
| pBluescript II KS (—) | *E. coli* cloning vector (Amp$^r$) | Stratagene |
| pTRCHIS2c | *E. coli* expression vector (Amp$^r$) | Invitrogen |
| Recombinant plasmids | | |
| pCKS120 | pBR328 toxin clone of stx$_{2c}$ | Lindgren et al. (1994) Infect. Immun. 62: 623-631 |
| pJES101 | pKS (—) toxin clone of stx$_{2e}$ | Samuel et al. (1990) Infect. Immun. 58: 611-618 |

TABLE 1-continued

Bacterial strains and plasmids used in this study.

| Strain or plasmid | Relevant characteristics | Source or reference |
|---|---|---|
| pSQ543 | pSK (—) toxin clone of $stx_{2dact}$ | Lindgren et al. (1994) Infect. Immun. 62: 623-631 |
| pMJS1 | pBluescript II KS (—) toxin clone of $stx_1$ | Smith et al. (2006) Vaccine 24: 4122-4129 |
| pMJS2 | pBluescript II KS (—) toxin clone of $stx_2$ | Smith et al. (2006) Vaccine 24: 4122-4129 |
| pMJS9 | pBluescript II KS (—) toxin clone, chimeric $stxA_1$-$stxA_2$ gene (StxA2 = amino acids 29-297 + StxB2) | This study |
| pMJS10 | pBluescript II KS (—) toxin clone, chimeric $stxA_1$-$stxA_2$ gene (StxA2 = amino acids 1-158) | This study |
| pMJS11 | pTrcHis2 C toxin clone, chimeric $stxA_1$-$stxA_2$ gene (StxA2 = amino acids 1-158) | This study |
| pMJS13 | pBluescript II KS (—) toxin clone, chimeric $stxA_1$-$stxA_2$ gene (StxA2 = amino acids 29-128) | This study |
| pMJS15 | pBluescript II KS (—) toxin clone, chimeric $stxA_1$-$stxA_2$ gene (StxA2 = aa 29-76) | This study |
| pMJS16 | pBluescript II KS (—) toxin clone, chimeric $stxA_1$-$stxA_2$ gene (StxA2 = amino acids 42-76) | This study |
| pMJS28 | pBluescript II KS (—) toxin clone, chimeric $stxA_1$-$stxA_2$ gene (StxA2 = amino acids 42-49) | This study |
| pMJS49 | pTrcHis2 C toxin clone of $stx_1$ | This study |
| pMJS49A | pTrcHis2 C toxin clone, chimeric $stxA_1$-$stxA_2$ gene (StxA2 = amino acids 42-49) | This study |
| pMJS49AB | pTrcHis2 C toxin clone, chimeric $stxA_1$-$stxA_2$ gene (StxA2 = amino acids 42-49, 96-100) | This study |
| pMJS49AC | pTrcHis2 C toxin clone, chimeric $stxA_1$-$stxA_2$ gene (StxA2 = amino acids 42-49, 244-259) | This study |
| pMJS49BC | pTrcHis2 C toxin clone, chimeric $stxA_1$-$stxA_2$ gene (StxA2 = amino acids 96-100, 244-259) | This study |
| pMJS49ABC | pTrcHis2 C toxin clone, chimeric $stxA_1$-$stxA_2$ gene (StxA2 = amino acids 42-49, 96-100, 244-259) | This study |
| pMJS50 | pTrcHis2 C toxin clone of $stx_2$ | Robinson et al. (2006) PNAS 103: 9667-9672 |
| pMJS52 | pTrcHis2 C toxin clone of $stx_{2c}$ | This study |
| pMJS59 | pTrcHis2 C toxin clone of $stx_{2d}$ | This study |
| pMJS49ABC* | pMJS49ABC with Y77S mutation | This study |

Construction of chimeric toxin plasmids.

Six chimeric toxin genes that contained portions of both $stxA_1$ and $stxA_2$ were generated by PCR with the splicing by overlap extension (SOE) protocol (Higuchi (1989) p. 61-70. In H. A. Erlich (ed.), PCR technology. Stockton Press, New York), and the PCR products were ligated into pBluescript II KS (–) (Stratagene, La Jolla, Calif.). The chimeric toxin genes contained the native promoters and Shine-Dalgarno sequences, and the levels of toxin expression from five of the clones were sufficient under those conditions. To increase the level of expression of the A subunit from one clone (pMJS11), the toxin operon was amplified by PCR a second time and an optimized Shine-Dalgarno sequence [TA<u>AGGAGGA</u>CAGCTATG (the optimized Shine-Dalgarno sequence is underlined and the translational start site for StxA2 is bolded) SEQ ID NO: 20] was added upstream of $stxA_2$. This latter PCR product was ligated into the pTrcHis2 C expression vector (Invitrogen, Carlsbad, Calif.) that has an isopropyl-β-D-thiogalactopyranoside (IPTG)-inducible promoter. All primers used in this study are listed in Table 2. The DNA sequence of each construct created for this study was confirmed prior to use.

TABLE 2

Synthetic oligonucleotide primers used in this study

| Primer | Sequence (5'-3')[a,b] | Purpose/region of homology |
|---|---|---|
| MJS1 | GATC<u>GGATCC</u>CCCTGTAACGAAGTTTGCGTAACAGC (SEQ ID NO: 21) | $stx_1$ upstream primer, used to generate pMJS9, pMJS13, pMJS15, pMJS16 and pMJS28 |

TABLE 2-continued

Synthetic oligonucleotide primers used in this study

| Primer | Sequence (5'-3')[a,b] | Purpose/region of homology |
|---|---|---|
| MJS2 | GATCGAATTCTCGCTTACGATCATCAAAGAGATC ATACC(SEQ ID NO: 22) | $stx_1$ downstream primer, used to generate pMJS10, pMJS11, pMJS13, pMJS15, pMJS16 and pMJS28 |
| MJS5 | GATCGGATCCAGCAAGGGCCACCATATCACATAC CGCC (SEQ ID NO: 23) | $stx_2$ upstream primer, used to generate pMJS10 |
| MJS6 | CAGGGGAATTCACCATGCGAATTTTTTTAACAA ATGC (SEQ ID NO: 24) | $stx_2$ downstream primer, used to generate pMJS9 |
| 2A29F | GAACATATATCTCAGGGGACCAC (SEQ ID NO: 25) | Used with 1A28R to generate pMJS9, pMJS13 and pMJS15 |
| 1A28R | GTGGTCCCCTGAGATATATGTTCTAATGGAGTAC CTATTGCAGAGCG (SEQ ID NO: 26) | Used with 2A29F to generate pMJS9, pMJS13 and pMJS15 |
| 1A159F | TTACGTTTGTTACTGTGACAGCTGAAGC (SEQ ID NO: 27) | Used with 2A158R to generate pMJS10 and pMJS11 |
| 2A158R | GCTTCAGCTGTCACAGTAACAAACCGTAAAACTG CTCTGGATGCATCTCTGGT (SEQ ID NO: 28) | Used with 1A159F to generate pMJS10 and pMJS11 |
| 1A129F | CAGATAAATCGCCATTCGTTGA (SEQ ID NO: 29) | Used with 2A128R to generate pMJS13 |
| 2A128R | TCAACGAATGGCGATTTATCTGCATTCCGGAACG TTCCAGCGC (SEQ ID NO: 30) | Used with 1A129F to generate pMJS13 |
| 2A42F | GGTACGTCTTTACTGATGATTAACCACACCCCAC CGGGCAGTTATTTTGC (SEQ ID NO: 31) | Used with 1A41R to generate pMJS16 |
| 1A41R | GCAAAATAACTGCCCGGTGGGGTGTGGTTAATCA TCAGTAAAGACGTACC (SEQ ID NO: 32) | Used with 2A42F to generate pMJS16 |
| 1A77F | TATGTGACAGGATTTGTTAACAGGAC (SEQ ID NO: 33) | Used with 2A76R to generate pMJS15 |
| 2A76R | GTCCTGTTAACAAATCCTGTCACATATAAATTAT TTTGCTCAATAATCAGACGAAGATGG (SEQ ID NO: 34) | Used with 1A77F to generate pMJS15 |
| 1A51 | AGGAGGACAGCTATGAAAATAATTATTTTTAGAG TGCTA (SEQ ID NO: 35) | $stxA_1$ upstream primer #1 with optimized Shine-Dalgarno sequence, used to generate pMJS49 |
| 1A52 | GATCGGATCCTAAGGAGGACAGCTATGA1AATAA TT (SEQ ID NO: 36) | $stxA_1$ upstream primer #2 with optimized Shine-Dalgarno sequence, used to generate pMJS49 |
| 1BC1 | GGTGGTGGTGACGAAAAATAACTTCGCTGAATCC (SEQ ID NO: 37) | $stxB_1$ His-tagged downstream primer #1, used to generate pMJS49 |
| 1BC2 | CAGTGGTGGTGGTGGTGACGAAAAATAAC (SEQ ID NO: 38) | $stxB_1$ His-tagged downstream primer #2, used to generate pMJS49 |
| BC3 | CATCGAATTCTCAGTGGTGGTGGTGGTGGTG (SEQ ID NO: 39) | $stxB_1$ His-tagged downstream primer #3, used to generate pMJS49 and pMJS52 |
| MSAF | AACCACACCCCACCGGGCAGTTATTTTGCAGTTG ATGTCAGAGGG (SEQ ID NO: 40) | Used with MSAR to generate pMJS28, pMJS49A, pMJS49AB, pMJS49AC and pMJS49ABC |
| MSAR | ATAACTGCCCGGTGGGGTGTGGTTAATCATCAGT AAAGACGTACC (SEQ ID NO: 41) | Used with MSAF to generate pMJS28, pMJS49A, PMJS49AB, pMJS49AC and pMJS49ABC |
| 96100F | ACACATATATCAGTGCCAGGTACAACAGCGGTTA CATTGTCTGG (SEQ ID NO: 42) | Used with 96100R to generate pMJS49AB, pMJS49BC and pMJS49ABC |
| 96100R | ACCTGGCACTGATATATGTGTAAAATCAGCAAAG CGATAAAAACA (SEQ ID NO: 43) | Used with 96100F to generate pMJS49AB, pMJS49BC and pMJS49ABC |
| JCT1F | GTGAATGAAGAGAGTCAACCAGAATGTCCGGCAG ATGGAAGAGTCCG (SEQ ID NO: 44) | C region primer #1, used with JCT1R to generate pMJS49AC, pMJS49BC and pMJS49ABC |

TABLE 2-continued

Synthetic oligonucleotide primers used in this study

| Primer | Sequence (5'-3')[a,b] | Purpose/region of homology |
|---|---|---|
| JCT1R | TTCTGGTTGACTCTCTTCATTCAC (SEQ ID NO: 45) | C region primer #1, used with JCT1F to generate pMJS49AC, pMJS49BC and pMJS49ABC |
| JCT2F | GGCATTAATACTGAATTGTCATCATCAGGGGCG CGTTCTGTTCGC (SEQ ID NO: 46) | C region primer #2, used with JCT2R to generate pMJS49AC, pMJS49BC and pMJS49ABC |
| JCT2R | ATGATGACAATTCAGTATTAATGCC (SEQ ID NO: 47) | C region primer #2, used with JCT2F to generate pMJS49AC, pMJS49BC and pMJS49ABC |
| 2A51 | AGGAGGACAGCTATGAAGTGTATATTATTTAAAT GGGT (SEQ ID NO: 48) | $stxA_2$ upstream primer #1 with optimized Shine-Dalgarno sequence, used to generate pMJS11 and pMJS52 |
| 2A52 | GATC<u>GGATCC</u>TAAGGAGGACAGCTATGAAGTGTA (SEQ ID NO: 49) | $stxA_2$ upstream primer #2 with optimized Shine-Dalgarno sequence, used to generate pMJS11 and pMJS52 |
| C12B | GGTGGTGGTGGTCATTATTAAACTGCACTTC (SEQ ID NO: 50) | $stxB_2$ His-tagged downstream primer #1, used to generate pMJS52 |
| C22B | CAGTGGTGGTGGTGGTGGTCATTATTAAA (SEQ ID NO: 51) | $stxB_2$ His-tagged downstream primer #2, used to generate pMJS52 |
| 2dF | GATC<u>GGATCC</u>CTGGTATCGTATTACTTCAGCC (SEQ ID NO: 52) | Used with 2dR to generate pMJS59 |
| 2dR | GATC<u>GAATTC</u>CTGCACACTACGAAACCAGC (SEQ ID NO: 53) | Used with 2dF to generate pMJS59 |
| 1Y77SF | TCAGTGACAGGATTTGTTAACAGGAC (SEQ ID NO: 54) | Used with 1Y77SR to generate pMJS49ABC* |
| 1Y77SR | GTCCTGTTAACAAATCCTGTCACTGATAAATTAT TTCGTTCAACAATAAGCCG (SEQ ID NO: 55) | Used with 1Y77SF to generate pMJS49ABC* |

[a]Restriction enzyme sites are underlined.
[b]Mutagenic codon sites are in bold.

Five additional His-tagged chimeric toxins were generated from an $stx_1$ clone that contained six histidine codons immediately downstream of the B gene (FIG. 2A). The toxins produced by these chimeras contain one, two, or three regions from the Stx2 A subunit (hereafter referred to as regions A, B, and C) that comprise the putative 11E10 monoclonal antibody epitope in place of the comparable sequence in Stx1. Regions A, B, and C refer to amino acids 42-49 (SEQ ID NO: 1), 96-100 (SEQ ID NO: 2), and 244-259 (SEQ ID NO: 3), respectively, of the Stx2 A subunit. The five chimeric toxins made were named: Stx1+A (containing the chimeric Stx2 A sequence set forth in SEQ ID NO: 4), Stx1+AB (containing the chimeric Stx2 A sequence set forth in SEQ ID NO: 5), Stx1+AC (containing the chimeric Stx2 A sequence set forth in SEQ ID NO: 6), Stx1+BC (containing the chimeric Stx2 A sequence set forth in SEQ ID NO: 7), or Stx1+ABC (containing the chimeric Stx2 A sequence set forth in SEQ ID NO: 8).

Generation and purification of partially toxoided Stx1+ABC.

The Stx1+ABC toxin was partially toxoided by changing the tyrosine residue at position 77 of the A subunit to a serine residue by the SOE protocol. The Y77S mutation decreased the 50% cytotoxic dose ($CD_{50}$) for Vero cells from $10^6$ to $10^2$ $CD_{50}$s per ml of induced culture. This 4-log reduction in cytotoxicity after the Y77S mutation was introduced is similar to that which has been previously reported for the Y77S mutation in Stx1 (Deresiewicz et al. (1992) *Biochemistry* 31:3272-3280).

The Stx1+ABC toxoid was purified with a nickel affinity column as previously described (Smith et al. (2006) *Infect. Immun.* 74:6992-6998). The concentration of the toxoid was determined by bicinchoninic acid assay (Pierce, Rockford, Ill.). A silver-stain of a sodium dodecyl sulfate-polyacrylamide gel revealed that the A and B subunits of the chimeric toxoid were the two major bands present, although other minor bands were observed (data not shown).

Construction of Stx2c and Stx2d variant clones.

A clone that expressed His-tagged Stx2c was created by PCR as previously described for Stx2 (Robinson et al. (2006) *Proc. Natl. Acad. Sci. U.S.A* 103:9667-9672). The $stx_{2d}$ clone was generated by PCR from *E. coli* EH250 with primers 2DF and 2DR (Pierard et al. (1998) *J. Clin. Microbial.* 36:3317-3322). The PCR product was ligated into the expression vector pTrcHis2 C. That $stx_{2c}$ and $stx_{2d}$ were amplified correctly was confirmed by sequence analyses.

Western Blot Analyses

Purified Stx1, Stx2, or sonic lysates of bacteria that expressed chimeric Stx1/Stx2 toxins were subjected to sodium dodecyl sulfate-polyacrylamide gel electrophoresis (SDS-PAGE) and then examined by Western blot as previously described (Smith et al., supra). The concentrations of the A subunits in sonic lysates that contained Stx1, Stx2, or the chimeric toxins were estimated as follows. First, the specific dilutions of rabbit anti-Stx1 and anti-Stx2 rabbit polyclonal antibodies that detected the purified A subunits from Stx1 or Stx2, respectively, to relatively equivalent levels were determined through the use of NIH Image J software, http://rsb.info.nih.gov/nih-image. Second, the chimera-containing sonic lysates were separated by SDS-PAGE, the resulting gels were then transferred to nitrocellulose, and those blots then probed with a mixture of rabbit anti-Stx1 and anti-Stx2 rabbit polyclonal antibodies diluted as determined above. Third, the bands that corresponded to the chimeric A subunits in each lane were quantified with the NIH Image J program to determine the toxin concentration in each lysate sample. Fourth, two additional polyacrylamide gels were loaded with purified Stx1, Stx2 or samples of the chimera-containing lysates normalized to contain equivalent concentrations (as determined from step 3). The toxin preparations were then subjected to SDS-PAGE followed by Western blot analysis with a mixture of rabbit anti-Stx1 and rabbit anti-Stx2 polyclonal antibodies (FIG. 1B top panel) (blot 1) or 11E10 monoclonal antibody (FIG. 1B bottom panel)(blot 2). The secondary antibodies used in these Westerns were goat anti-rabbit Immunoglobulin G (IgG) conjugated to Horseradish peroxidase [(HRP) Bio-Rad, Hercules, Calif.] at a dilution of 1:15,000 for blot 1 (FIG. 1B top panel) and goat anti-mouse IgG conjugated to HRP (Bio-RAD, Hercules, Calif.) at a dilution of 1:3,000 for blot 2 (FIG. 1B bottom panel). The bound secondary antibodies were detected by chemiluminescence with the ECL-Plus Western blotting detection kit (Amersham Bioscience, Little Chalfont, Buckinghamshire, England).

Western blots were also performed on sonic lysates of clones that expressed Stx2, Stx2c, Stx2d, Stx2$d_{act}$ or Stx2e. First, the concentration of the A subunits from these toxin samples was determined as described above, except that only rabbit anti-Stx2 polyclonal antibodies was used as a probe. Then two additional polyacrylamide gels were loaded with equivalent quantities of the normalized samples, and Western blots were conducted with either rabbit anti-Stx2 polyclonal antibodies or the 11E10 monoclonal antibody as the primary antibodies. The secondary antibodies and method of detection were the same as described above.

In vitro neutralization assays on Vero cells.

In vitro neutralization assays of sonic lysates from bacteria that contained Stx1, Stx2, the chimeric Stx1/Stx2 toxins, Stx2c, Stx2d, Stx$2_{dact}$, or Stx2e were carried out with 11E10 on Vero cells (ATCC, Manassas, Va.) as described previously (Marques et al. (1986) *J Infect. Dis.* 154:338-341; Smith et al., supra). In brief, equal volumes of samples that contained toxin (one to three $CD_{50}$s) in Eagle's Minimal Essential Medium (EMEM) and purified 11E10 monoclonal antibody (0.5 mg/ml) in EMEM were mixed together and incubated for 2 h at 37° C. and 5% $CO_2$. The toxin-antibody mixture was then overlaid onto subconfluent Vero cells in 96-well plates and incubated for 48 h. The Vero cells were then fixed, stained, and the optical density at 600 nm ($OD_{600}$) was determined. These neutralization experiments were done at least twice in duplicate. The capacity of the 11E10 monoclonal antibody to neutralize the cytotoxic effect of the toxin in the sonic lysates was determined by comparing the cell viability in wells in which toxin alone or toxin and antibody were added. The percent neutralization of the toxins by the antibody was calculated by the following formula. Percent neutralization: [(Average $OD_{600}$ of toxin+Antibody wells−Average $OD_{600}$ of toxin only wells)/(Average $OD_{600}$ of cells only wells−Average $OD_{600}$ toxin only wells)]×100. The 11E10 monoclonal antibody neutralized Stx2 to about 65% of wild-type activity. To make it easier to compare the percent neutralization levels of the toxin derivatives by the 11E10 monoclonal antibody, the data were normalized such that the amount of neutralization of Stx2 by 11E10 was set to 100%, and the neutralization levels of the other toxins were calculated relative to that of Stx2.

Immunization and Challenge of Mice

Preimmune sera were collected from CD-1 male mice that weighed 14-16 g (Charles River Laboratories, Boston, Mass.). These serum samples were used in enzyme-linked immunosorbent assays (ELISA) to determine if the mice had pre-existing titers to Stx1 or Stx2. None of the mice showed an immune response to either toxin at the start of the study. The mice were then divided into two groups: a sham-inoculated group (hereafter called negative-control group) and a group that was immunized with the chimeric toxoid. Mice in the negative control group were immunized intraperitoneally with a mixture of PBS and TiterMax, a water-in-oil-adjuvant (TiterMax, USA Inc., Norcross, Ga.). The second group of mice was immunized intraperitoneally with 1 ug of toxoid mixed with TiterMax. The mice were boosted at 3-week intervals for a total of four boosts. Two weeks after the last boost, five negative-control mice and five toxoid-immunized mice were challenged intraperitoneally with 10 times the 50% lethal dose ($LD_{50}$) of Stx1 (1,250 ng), and 29 negative control mice and 34 toxoid-immunized mice were challenged with 5 $LD_{50}$s of Stx2 (5 ng).

In vitro protein synthesis inhibition assays.

Rabbit reticulocyte lysate, firefly luciferase mRNA, and luciferin substrate were purchased from Promega Corporation (Madison, Wis.). Stx2 (4 ng/μl) was combined with an equal volume of antibody (at 4 or 40 ng/μl), and 1 μl of the toxin/antibody mixture was combined with 9 μl reticulocyte lysate. The mixture was incubated at 30° C. to allow toxin to inactivate ribosomes in the lysate. After 1 hour, an aliquot of luciferase mRNA and amino acids that had been heated to 70° C. for 2 min was added, and the solution was incubated for an additional 90 min to allow the in vitro protein synthesis to proceed. All assays were done in triplicate. Luciferase activity was measured by adding 1 μl of the lysate mixture to 20 μl of luciferin substrate in clear 96 well plates (Fisher Scientific, Pittsburgh, Pa.). Bioluminescent light emission was detected with a Kodak Image Station 440CF in a 10 min exposure. Luminescent signal was analyzed by summation of total signal intensity within a circular area that corresponded to a single well.

Localization of 11E10 in Intoxicated Cells

Vero cells were seeded in 8 well tissue culture slides (Thermo Fisher Scientific, Rochester, N.Y.) at a concentration of $1\times10^5$ cells/ml and allowed to adhere for 24 hrs at 37° C. in an atmosphere of 5% $CO_2$. Stx2 (0.2 ml of 10 ng/ml) was mixed with 10 ng of purified 11E10 monoclonal antibody or with PBS as a negative control. The antibody/toxin or PBS/toxin solutions were incubated with Vero cells for 6 h, and then the cells were fixed with buffered formalin (Formalde-Fresh, Fisher Scientific, Pittsburgh, Pa.) and permeabilized with 0.001% Triton-X100 (Pierce, Rockford, Ill.) in PBS. All immunostaining procedures were done in PBS with 3% bovine serum albumin (BSA, Sigma, St. Louis Mo.). The presence of monoclonal antibody 11E10 within the cells was detected with Alexa-Fluor 488 labeled donkey anti-mouse IgG (Invitrogen, Carlsbad, Calif.). Total Stx2 within the intoxicated cells was labeled with rabbit anti-Stx2 polyclonal antibodies, and Alexa-Fluor 488-conjugated donkey anti-rabbit IgG was used as the secondary antibody (Invitrogen, Carlsbad, Calif.). Stx2 and endosome double labeling was accomplished with anti-Stx2 monoclonal antibody 11F11 (Perera et al., supra), BEI Resources, Manassas, Va.) and anti-EEA1 (C-15) goat polyclonal antibodies (Santa Cruz Biotechnology, Santa Cruz, Calif.), respectively, and Alexa-Fluor labeled secondary antibodies. After incubation with the appropriate primary and secondary antibodies, the cells were fixed with formalin for 20 min at 37° C., and the slides were mounted with SlowFade medium (Invitrogen, Carlsbad, Calif.). Images at 40× magnification of the bound fluorophore-labeled secondary antibodies were obtained via an Olympus microscope with reflected light fluorescence attachment and a Spot CCD digital camera (Diagnostic Instrument Products, Sterling Heights, Mich.). Fluorescence images were processed and overlaid with Adobe Photoshop (Adobe Systems, San Jose, Calif.).

Results

Interaction of initial chimeric toxins with monoclonal antibody 11E10.

Figure 1B:
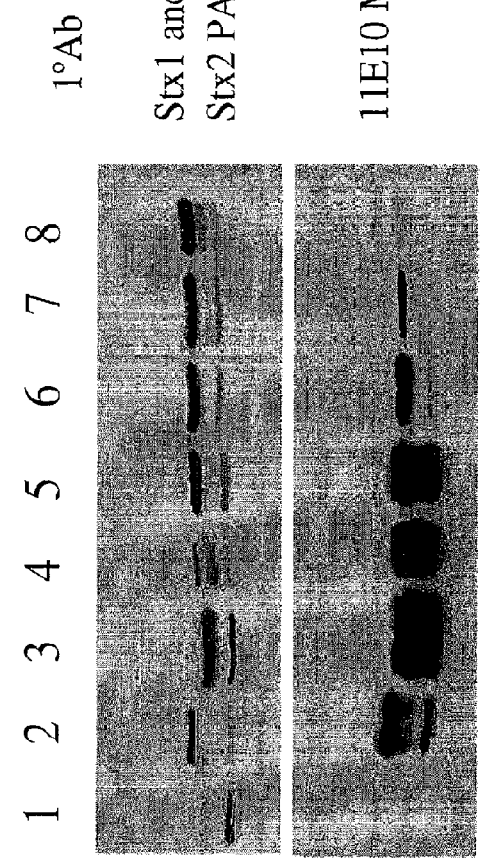
FIG. 1B shows Western blot analyses of Stx1, Stx2 and the initial chimeric toxins probed with rabbit anti-Stx1 and anti-Stx2 polyclonal (top panel) or monoclonal 11E10 (bottom panel). Lanes 1 and 2 contain 25 ng of purified Stx1 or Stx2 respectively. Lanes 3 to 8 contain the following chimeric toxins: lane 3, Stx1(2A$_{29-297}$); lane 4, Stx1(2A$_{1-158}$); lane 5, Stx1(2A$_{29-128}$); lane 6, Stx1 (2A$_{29-76}$); lane 7, Stx1(2A$_{42-76}$); lane 8, Stx1 (2A$_{42-49}$).

To determine the portion of Stx2 that interacts with the 11E10 monoclonal antibody, we constructed an initial set of six chimeric toxin operons that contained different regions of the stxA$_2$ gene inserted in place of the corresponding region of stxA$_1$ (FIG. 1A). Western blots of purified Stx1, Stx2, or lysates from *E. coli* DH5α that express one of the six different chimeric Stx1/Stx2 toxins were probed with the 11E10 monoclonal antibody. The antibody reacted strongly with Stx2 and the chimeric toxins that contained the amino acids from the following regions of the Stx2 A subunit: 29-297, 1-158, and 29-128 (FIG. 1B). The chimeric toxin with the minimal portion of Stx2 that was still recognized by 11E10, albeit weakly, contained just eight amino acids from StxA2, region 42-49.

Figure 1C:
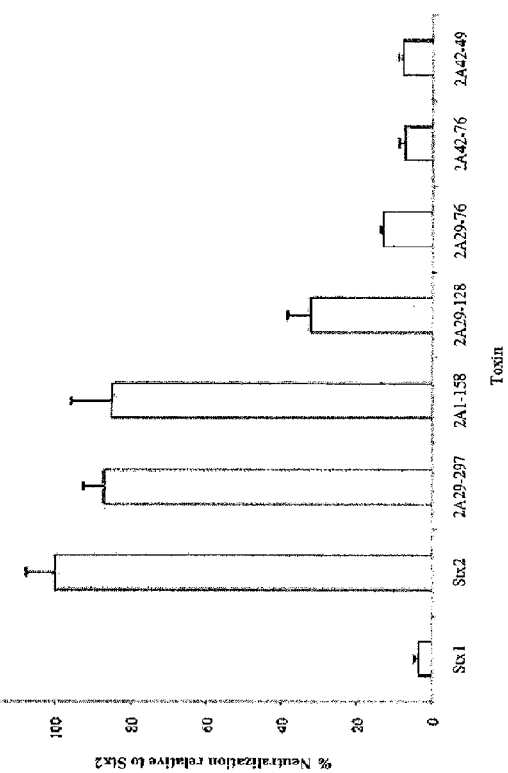
FIG. 1C shows the percent neutralization of the initial chimeric toxins with the 11E10 monoclonal antibody. The neutralization data were normalized such that the % neutralization of full-length Stx2 was set to 100% (actual % neutralization=65%) and the neutralization levels for the rest of the toxins are given as a percent of the normalized full-length Stx2 neutralization. The error bars represent the standard error of the normalized values.

Next, the capacity of the 11E10 monoclonal antibody to neutralize the toxicity of bacterial lysates that contained Stx1, Stx2, or one of the six initial chimeric toxins for Vero cells was examined. As expected, the 11E10 monoclonal antibody neutralized Stx2 but did not neutralize Stx1 (FIG. 1C). However, the hybrid toxins with region 1-158 or 29-297 from StxA2 were about 85% neutralized by 11E10 compared to Stx2, a result that suggested that important components of the 11E10 epitope lie between residues 29-158 of Stx2. In contrast, the chimeric toxin with amino acids 29-128 from Stx2 was recognized strongly in the immunoblot but was only neutralized to about 32% of the level of Stx2. Together these findings suggest that the 11E10 neutralizing epitope encompasses a larger number of amino acids than are required for binding of 11E10 to Stx1(2A$_{29-128}$) in a Western blot and, therefore, that a portion of the neutralizing epitope is missing from this hybrid. The other three chimeric toxins that were weakly detected by the 11E10 monoclonal antibody in the Western blot analysis were not appreciably neutralized by 11E10 (less than 15%) when compared to the normalized level of Stx2 neutralization. Taken together, these results indicate that one or more key components of the 11E10 neutralizing epitope on Stx2 exist outside of amino acids 29-76.

Analyses of differences between the Stx1 and Stx2 a subunit amino acid sequences and crystal structures.

The Western blot and neutralization analyses of the first set of chimeric toxins indicated that the 11E10 epitope required at least amino acids 42-49 of the Stx2 A subunit (SEQ ID NO: 1) for toxin detection but also revealed that additional amino acids were needed for full recognition and toxin neutralization. Therefore, the amino acid sequences of the mature A subunits from Stx1 and Stx2 were aligned to identify additional unique stretches of amino acids that might be involved in recognition and neutralization of Stx2 by 11E10. Next, the crystal structures of Stx (Fraser et al. (1994), supra) and Stx2 (Fraser et al. (2004), supra) (Protein Data Bank accession numbers 1RQ4 and 1R4P, respectively) were compared using the Deep View/Swiss-PDB viewer to assess the location of regions of sequence differences between the toxins in the three dimensional structures and the proximity of such regions to each other. As established earlier, the eight amino acids that span residues 42-49 in the Stx2 A subunit form part of the 11E10 binding site and are hereafter referred to as region A or SEQ ID NO: 1 (FIG. 2A; Region A underscored amino acids). When the eight amino acids from region A were viewed in the context of the Stx2 crystal structure, they appeared to form a major bend in the toxin structure (as indicated in green and by a black arrow in FIG. 2B and also as indicated in FIG. 2C) and, in addition, were found on the outside face of Stx2, near the active site cleft around amino acid 167.

Figure 2C:
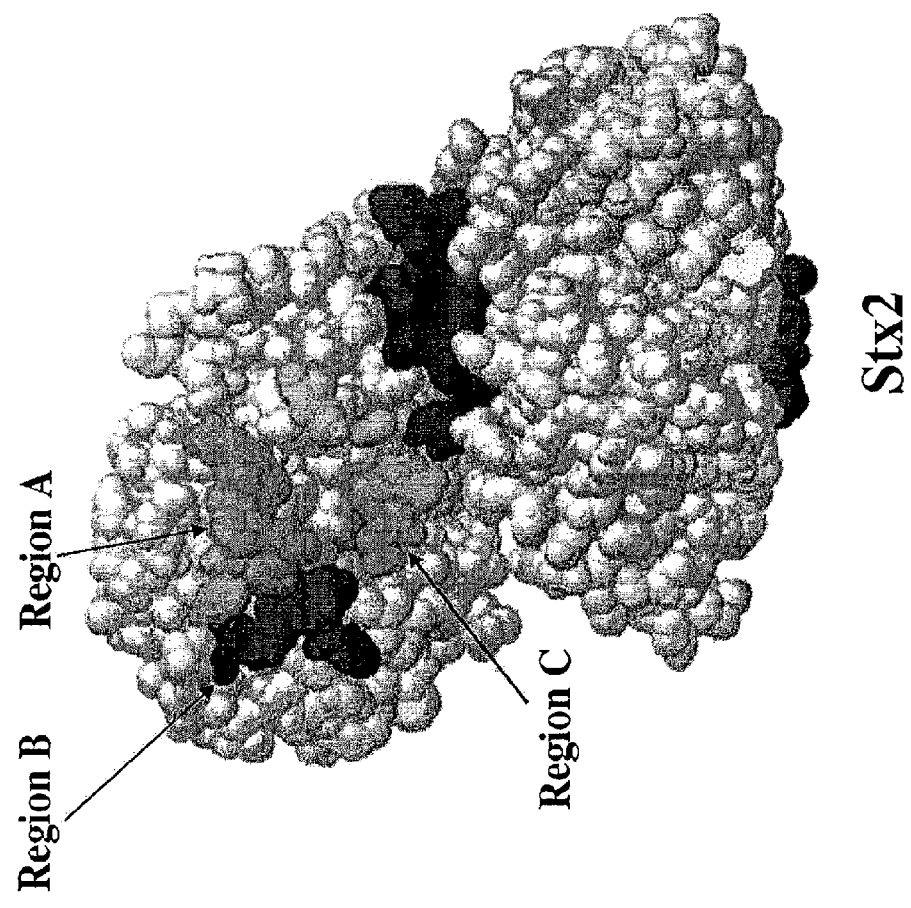
FIG. 2C shows a spacefill representation of the Stx2 crystal structure. Regions A, B, and C are indicated with arrows.

A second dissimilar area between the A subunits of Stx1 and Stx2 was identified when the amino acid sequences and the crystal structures of these two toxins were compared, a segment we called region B or SEQ ID NO: 2 (see FIG. 2A; Region B underscored amino acids). Region B spans five residues in the A subunit of Stx2 ($_{96}$THISV$_{100}$) (SEQ ID NO: 2) and four out of the five amino acids in this region differ between Stx1 and Stx2 (FIG. 2A). Although region B is approximately 50 amino acids away from region A, this portion of amino acids extends toward region A in the Stx2 crystal structure (region B is indicated in blue and by a gray arrow in FIG. 2B). The close proximity of region A to region B in a three-dimensional structure is even more apparent in a space-filling model (FIG. 2C).

The third dissimilar area between the A subunits of Stx1 and Stx2, which we named region C or SEQ ID NO: 3, overlaps the furin cleavage site around residue 246 of Stx2 (see FIG. 2A; Region C underscored amino acids). Region C was identified not only because of amino acid sequence differences between Stx1 and Stx2 in that location, but also because comparison of the crystal structures of Stx and Stx2 indicated that region C (as indicated in cyan and by a white arrow in FIG. 2C) was in spatial proximity to regions A and B. From our analyses of the Stx and Stx2 crystal structures we concluded that regions A, B, and C cluster on the same face of Stx2 relatively near the catalytic active site (as best seen in FIG. 2C).

Interaction of the second generation chimeric toxins with monoclonal antibody 11E10.

Figure 3A:
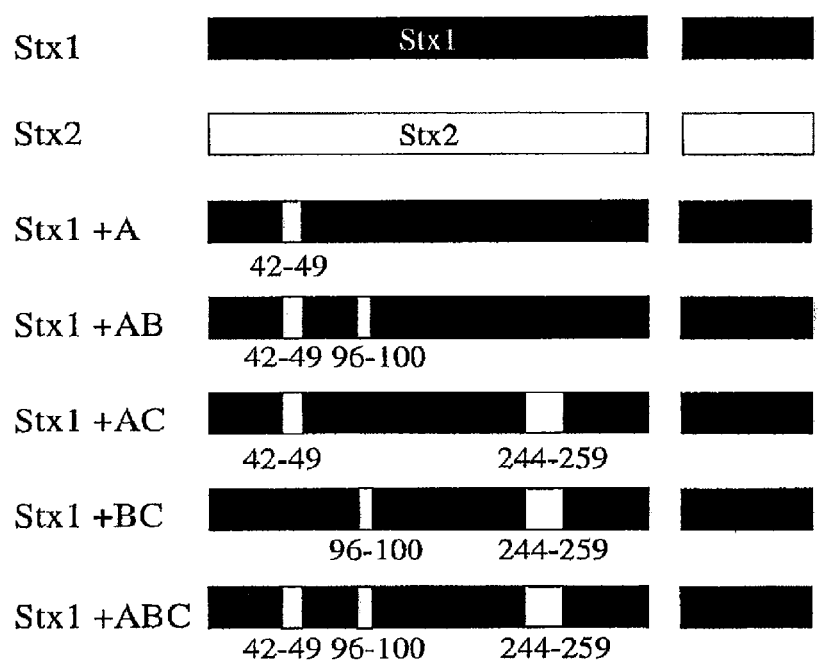
FIG. 3A illustrates second generation chimeric toxins that contain chimeric A subunits. Stx1 is presented in black, while Stx2 is depicted in white. The names of the chimeric toxins are shown to the left of the respective chimeric proteins and the regions of Stx2 are listed beneath the chimeric A subunits. Region A, B, and C refer to amino acids 42-49 (SEQ ID NO: 1), 96-100 (SEQ ID NO: 2), 244-259 (SEQ ID NO: 3), respectively of StxA2.
Figure 3B:
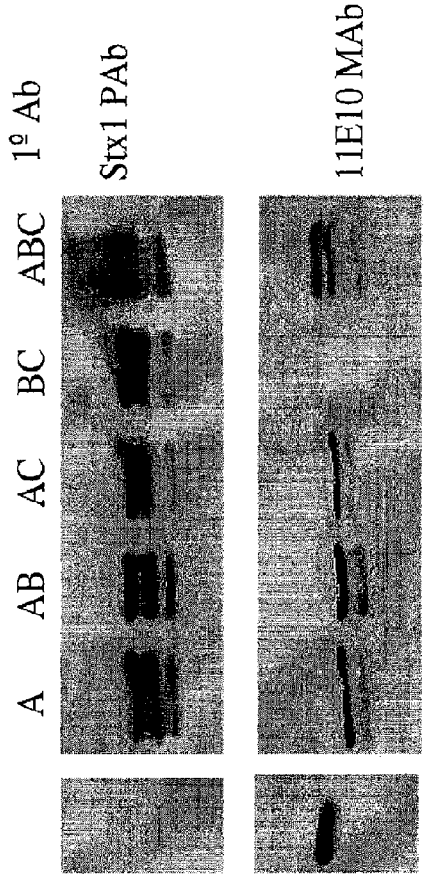
FIG. 3B depicts Western blot analyses of Stx1, Stx2, and the five second generation chimeric toxins probed with rabbit anti-Stx1 (top panel) or the 11E10 monoclonal antibody (bottom panel). Lane 1 contains 25 ng of purified Stx2. Lanes 2 to 6 contain the following chimeric toxins: lane 2, Stx1+A; lane 3, Stx1+AB; lane 4, Stx1+AC; lane 5, Stx1+BC; lane 6, Stx1+ABC.

To determine whether regions B and C were part of the 11E10 epitope, we produced a second set of chimeric toxins that contained various combinations of regions A, B, or C from Stx2 in place of the corresponding regions on Stx1 (FIG. 3A). Next, Western blots of Stx1, Stx2 or the chimeric toxins were probed with 11E10 (FIG. 3B, bottom panel). The 11E10 monoclonal antibody detected all of the toxins that contained region A (Stx2, Stx1+A, Stx1+AB, Stx1+AC, and Stx1+ABC) (FIG. 3B, bottom panel). The toxins missing region A were not detected by the 11E10 monoclonal antibody (Stx1 and Stx1+BC), a finding that confirms that region A is an essential component of the 11E10 epitope. However, the two chimeric toxins that incorporated regions A and B (Stx1+AB or Stx1+ABC) appeared to be more strongly detected by the 11E10 monoclonal antibody than chimeric toxins that included region A alone or A combined with region C (FIG. 3B, bottom panel). Collectively, these results indicate that both regions A and B are important for full 11E10 recognition of the toxin.

Figure 3C:
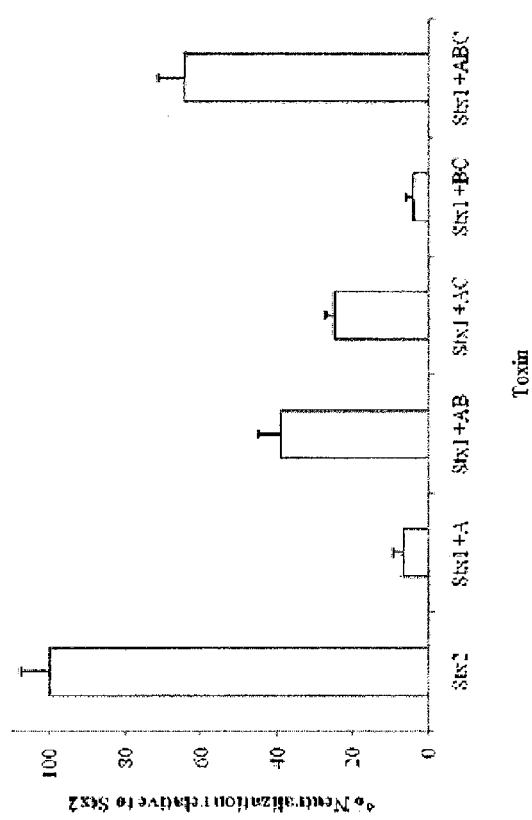
FIG. 3C shows neutralization of the second generation hybrid toxins by the 11E10 monoclonal antibody. The level of Stx2 neutralization was normalized to 100% as in FIG. 1C. The error bars represent the standard error of the normalized values.

We next assayed sonic lysates of each of the five second generation chimeric toxins (FIG. 3A) for in vitro neutralization by the 11E10 monoclonal antibody. The antibody neutralized the chimeric toxin that contained regions A, B, and C (Stx1+ABC) to approximately 65% of the level of Stx2 neutralization. In contrast, the chimeric toxins that contained only regions A and B (Stx1+AB) or A and C (Stx1+AC) were neutralized to about half the neutralization level of the Stx1+ABC chimera, (FIG. 3C). No appreciable neutralization by 11E10 was observed against the Stx1+A or Stx1+BC chimeric toxins (approximately 6.9 and 4.3% respectively). Since more extensive (>50%) neutralization of the chimeric toxins required regions A, B, and C from Stx2, we concluded that all three regions (A, B, and C) are necessary for >50% neutralization by 11E10.

Western blot and in vitro neutralization assay results with Stx2 and Stx2 variants and the 11E10 monoclonal antibody.

Figure 4A:
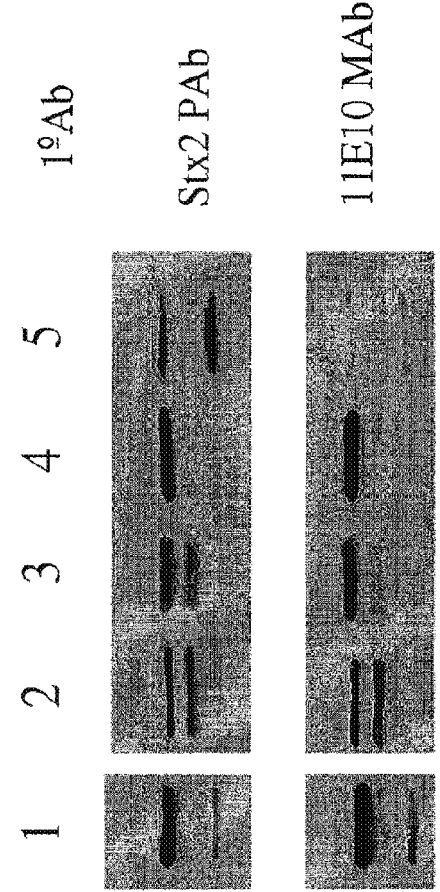
FIG. 4A shows Western blot analyses of Stx2 and Stx2 variants with the 11E10 monoclonal antibody. Lane 1 contains 25 ng of purified Stx2. Lanes 2 to 5 contain the following toxins: lane 2, Stx2c; lane 3, Stx2d; lane 4, Stx2d$_{act}$; lane 5, Stx2e. The Western blots were probed with either rabbit anti-Stx2 polyclonal antibodies (top panel) or the monoclonal antibody 11E10 (bottom panel).

To determine which of the Stx2 variants could be recognized and/or neutralized by 11E10, Stx1, Stx2, or the Stx2 variants (Stx2c, Stx2d, Stx2d$_{act}$ and Stx2e) were analyzed by Western blot. Stx2 and all of the Stx2 variants were recognized by 11E10, although Stx2e was detected to a much lesser extent (FIG. 4A, bottom panel). This weak detection of Stx2e by 11E10 in the Western blot format is consistent with our previous report that 11E10 was unable to detect Stx2e-producing strains by colony blot (Perera et al., supra). Stx2e has two conservative amino acid differences in region B as compared to Stx2 (AHISL (SEQ ID NO: 19) rather than THISV (SEQ ID NO: 2)). There are also several amino acid sequence differences immediately adjacent to region A (not shown). We conjecture that these differences may be responsible for the reduced recognition of Stx2e by 11E10 on Western blot.

Figure 4B:
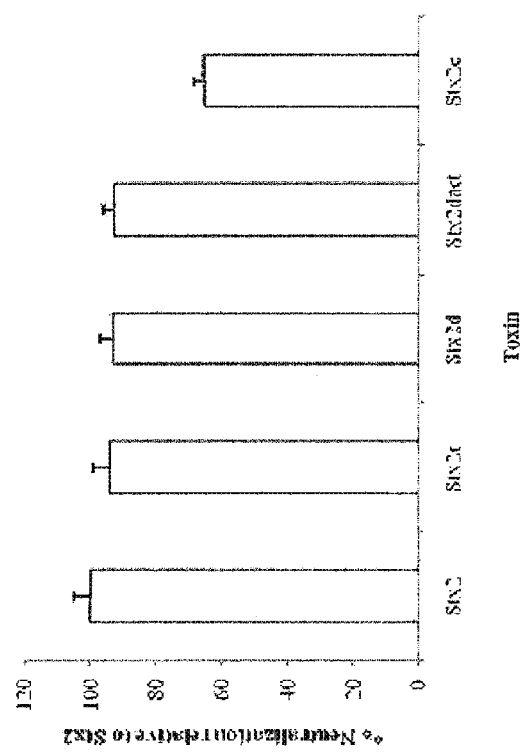
FIG. 4B depicts the percent neutralization by 11E10 of the Stx2 variants. The level of Stx2 neutralization was normalized to 100% as in FIG. 1C. The error bars represent the standard error of the normalized values.

When the neutralization capacity of monoclonal antibody 11E10 for the Stx2 variant toxins was evaluated, we found that 11E10 neutralized all the Stx2 variant toxins to greater than or equal to 60% of the level of neutralization of Stx2 (FIG. 4B). We were surprised at the level of neutralization observed by 11E10 of Stx2e because of the limited recognition of Stx2e by 11E10 in the Western blot format (FIG. 4A, bottom panel). However, the neutralization of Stx2e by 11E10 in this study agrees with our previous result that showed that 11E10 partially neutralizes Stx2e (Perera et al., supra).

Immune and protective response of the Stx1+ABC toxoid in mice.

We next sought to ascertain whether a toxoided derivative of the Stx1+ABC hybrid molecule could elicit a serum-neutralizing or protective response to Stx2 in mice. Groups of mice were immunized with the chimeric toxoid or PBS as a control. Serum from five toxoid-immunized mice and five PBS-immunized mice were then evaluated for an anti-Stx1 neutralizing response. None of the sera from the PBS-immunized mice contained Stx1-neutralizing activity. As expected from previous studies, all five toxoid-immunized mice had neutralizing antibodies directed against Stx1 (Smith et al. (2006) *Vaccine* 24:4122-4129, Wen et al., supra). The mean anti-Stx1 neutralization titer for the serum from these five mice was 4.0±0.9 logs above background. Eleven of the sera from the remaining 34 toxoid-immunized mice had some neutralizing response to Stx2, while none of the sera from the 29 PBS-immunized mice exhibited any anti-Stx2 response (data not shown).

Two weeks after the final boost, five negative-control mice and five toxoid-immunized mice were challenged intraperitoneally with 10 LD$_{50}$s of Stx1. All of the negative-control mice died while all of the toxoid-immunized mice survived the lethal challenge (Table 3), as predicted from the results of a previous study (Smith et al., supra, Wen et al., supra). In addition, the survival of the toxoid-immunized mice that were challenged with Stx1 directly correlated to the in vitro neutralizing titers from those mice.

TABLE 3

Protection of immunized mice against a lethal challenge with Stx1 or Stx2.

| Group | Mice immunized with: | Mice challenged with 10 LD$_{50}$$^{a,b}$ of: | Number of surviving mice/ total number of mice (percent survival) |
|---|---|---|---|
| A | PBS | Stx1 | 0/5 |
| B | Stx1 + ABC toxoid | Stx1 | 5/5 |
| C | PBS | Stx2 | 6/29 (20.7%) |
| D | Stx1 + ABC toxoid | Stx2 | 12/34 (35.3%)$^c$ |

$^a$The LD$_{50}$ was previously determined to be 125 and 1 ng/mouse for Stx1 and Stx2 respectively.
$^b$The average weight of the mice when they were challenged was 47.1 g.
$^c$Fisher's exact test was used to compare the proportions that survived in groups C and D and the p value was 0.2667.

Because low Stx2 neutralizing antibody titers were observed in the toxoid-immunized group, we chose to challenge the rest of the mice with only 5 LD$_{50}$s of Stx2. Six out of 29 negative-control mice (20.7%) survived the challenge with Stx2, while 12 out of 34 toxoid-immunized mice (35.3%) survived (Table 3), a finding that, while not statistically significant, suggests that the chimeric toxoid may have provided some protection from Stx2.

In vitro protein synthesis inhibition assay.

Figure 5:
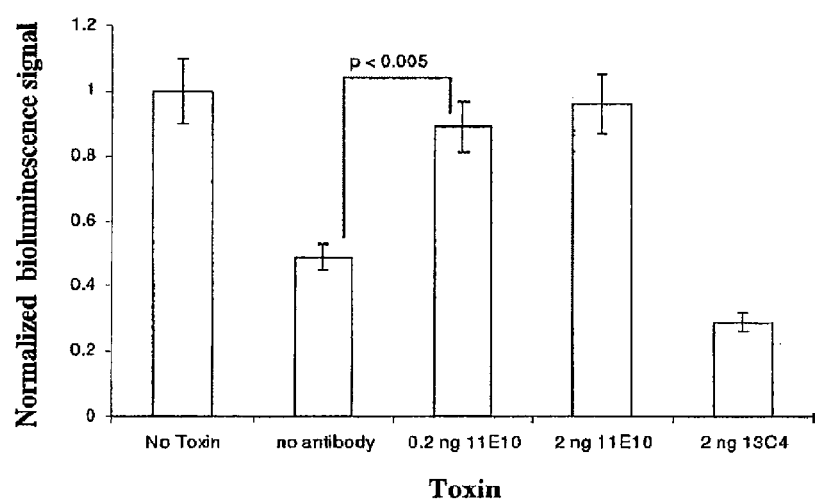
FIG. 5 depicts protein synthesis inhibition measured by translation of luciferase mRNA in rabbit reticulocyte lysate. A 0.2 ng aliquot of purified Stx2 was mixed with 0, 0.2, or 2 ng 11E10 and added to reticulocyte lysates. Protein synthesis inhibition was indicated by a reduction of translation of luciferase mRNA and was measured by bioluminescence after addition of the toxin-treated lysate to luciferin substrate. A 2 ng sample of the isotype-matched irrelevant antibody 13C4 was mixed with 2 ng Stx2 as a negative control. Error bars represent the 95% confidence interval calculated from the standard error of the means ratio. Probability values derived from a two-tailed Student's t-Test indicates a significant difference in bioluminescence signal between samples with and without antibody ($p<0.005$).

Our finding that the 11E10 epitope appeared to consist of surface loops around the Stx2 active site cleft led us to hypothesize that 11E10 might neutralize Stx2 by blocking the capacity of the toxin to inhibit protein synthesis. Therefore, we assessed whether the 11E10 monoclonal antibody could neutralize the ribosome-inactivating effects of Stx2 in a rabbit reticulocyte protein synthesis assay to which luciferase mRNA was added. A concentration of toxin was chosen that decreased the signal from the luciferase reporter protein by approximately 60% as compared to the signal measured when no toxin was added (FIG. 5). Addition of 11E10 to the assay allowed protein synthesis to occur in the rabbit reticulocyte lysate even when the Stx2 was present, whereas the isotype-matched irrelevant antibody did not (FIG. 5).

Monoclonal Antibody 11E10 Alters the Overall Distribution of Stx2 in Vero Cells

Figures 6A, 6B, 6C, 6D, 6E, 6F, 6G, 6H, 6I, 6J:
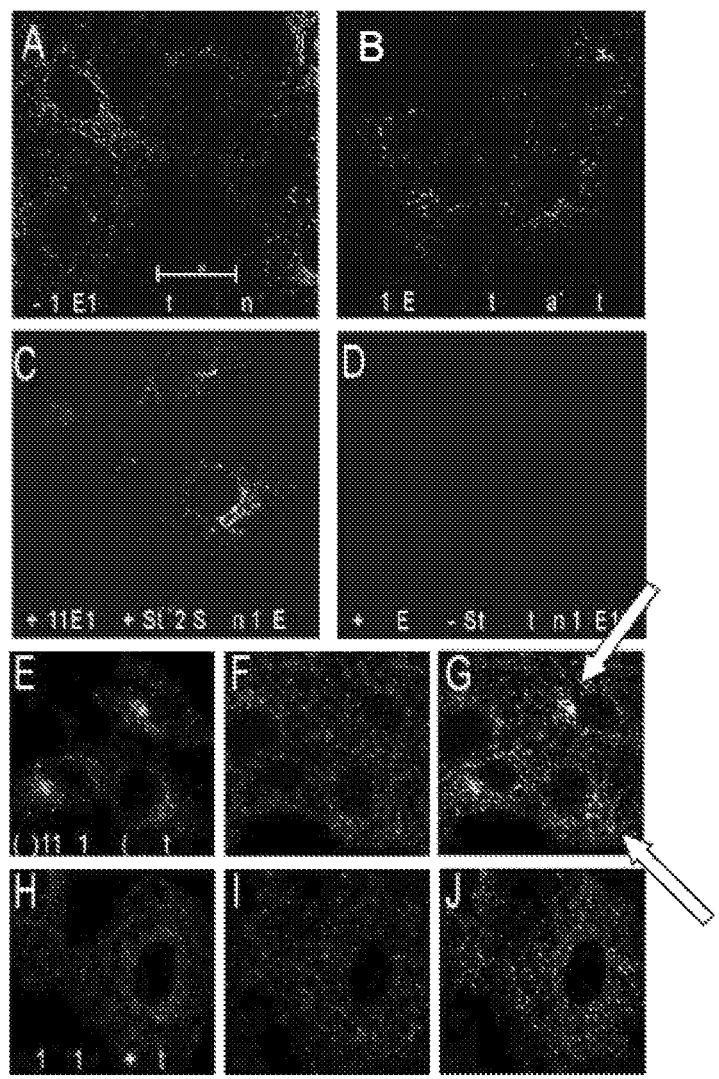
FIGS. 6A-6J shows that monoclonal antibody 11E10 alters the overall cellular distribution of Stx2 in Vero cells. Stx2 was mixed with PBS (A, H-J) or 11E10 (B, C and E-G) and then added to Vero cells for 6 h. As a control, 11E10 was added to Vero cells in the absence of Stx2 (D). The toxin was detected with polyclonal antibodies against Stx2 followed by secondary antibody conjugated with AlexaFlu antibody fragments such as Fabs, diabodies, and Fab' fragments), recombinant binding regions based on antibody binding regions, chimeric antibodies, primatized antibodies, humanized and fully human antibodies, domain deleted antibodies, and antibodies labeled with a detectable marker, or coupled with a toxin or radionuclide. Such antibodies are produced by conventional methods known in the art. In one aspect, the invention includes the preparation of monoclonal antibodies or antibody fragments that specifically bind to the 11E10 epitope of Stx2 where the preparation includes the use of a polypeptide which contains at least one, two, or three sequences selected from the sequences set forth in SEQ ID NOs: 1, 2, or 3. One or enzyme-linked immunoabsorbent assay (ELISA) or using a Biacore instrument. The binding affinity of the monoclonal antibody can, for example, be determined by the Scatchard analysis of Munson and Rodbard ((1980) *Anal Biochem.* 107: 220-239).

Although we found that monoclonal antibody 11E10 prevented the inhibition of protein synthesis by Stx2 in the in vitro protein synthesis assay, we further hypothesized that 11E10 may prevent Stx2 from reaching ribosomes in the cytoplasm of intoxicated Vero cells. We therefore sought to determine if monoclonal antibody 11E10 alters Stx2 localization in target cells. (We previously found that 11E10-bound Stx2 could bind to Vero cells and that 11E10 could attach to Stx2 bound to Vero cells (data not shown)). Stx2 was mixed with 11E10 or PBS and the antibody/toxin or PBS/toxin mixture was incubated with Vero cells. The distribution of Stx2 in the target cells was then visualized with rabbit polyclonal antibodies anti-Stx2 and a fluorophore-labeled anti-rabbit IgG secondary antibody (FIG. 6). Stx2 appeared to be distributed throughout the cytoplasm in the absence of 11E10 (FIG. 6A) but seemed to remain concentrated in largely perinuclear bodies in the presence of 11E10 (FIG. 6B). When the cells incubated with the toxin/

11E10 mixture were stained with anti-mouse IgG, 11E10 was observed in the same perinuclear punctate structures as Stx2 (FIG. 6C). The 11E10 monoclonal antibody was unable to enter cells in the absence of toxin (FIG. 6D). The localization of 11E10-bound Stx2 within punctate bodies around the nucleus suggested that the antibody-toxin complex entered the cell but did not traffic into the cytoplasm. We therefore asked if Stx2 or 11E10-bound Stx2 was localized in early endosomes by immunostaining the intoxicated cells with the early endosome marker monoclonal antibody EEA-1. We found that much of the Stx2 in cells intoxicated with 11E10-bound Stx2 colocalized with the early endosome marker (FIG. 6E-G), as shown by a yellow-orange color when the staining patterns were overlapped. In contrast, when Vero cells were incubated with Stx2 alone, the toxin was found throughout the cytoplasm and only a small amount colocalized with the early endosome marker (FIG. 6H-J).

Discussion

Our results demonstrate that the 11E10 monoclonal antibody epitope is conformational and include three non-linear regions in the Stx2 A subunit that appear close to the active site of the toxin in the crystal structure (see FIG. 2C). Our strategy to identify the 11E10 epitope involved the generation of chimeric Stx1/Stx2 toxins and was based on the assumption that placing Stx2 sequences onto the Stx1 backbone would maintain the 3-dimensional tertiary structure of the antibody epitope and allow recognition by the 11E10 monoclonal antibody. We found that the minimal region of StxA2 that allowed recognition by 11E10 in Western analysis consisted of only eight Stx2 amino acids ($_{42}$NHTPPGSY$_{49}$) (SEQ ID NO: 1). However, the chimeric Stx1/Stx2 with just those 8 amino acids from Stx2 (region A) was not neutralized by the 11E10 monoclonal antibody. Because 11E10 neutralizes Stx2, we considered that the 8 amino acids we had identified consisted of a critical region of the 11E10 epitope but did not comprise the complete neutralizing epitope. We further analyzed differences in both the amino acid sequences and crystal structures of Stx1 and Stx2 to try to identify additional regions on Stx2 that might be involved in 11E10 recognition and neutralization. Through these comparisons, we identified two more segments of Stx2 that could potentially contribute to the 11E10 epitope. Indeed, we found that all three regions were required for the most complete recognition and neutralization by 11E10 when those regions were used to replace the corresponding segments on Stx1.

Our conclusion that the complete 11E10 neutralizing epitope comprises three non-continuous regions on Stx2 is perhaps surprising because the monoclonal antibody recognizes Stx2 under the putatively denaturing conditions of a Western blot. Several explanations for this latter observation are conceivable. These possibilities include that the Western reactivity is primarily due to the interaction of 11E10 with region A ($_{42}$NHTPPGSY$_{49}$) or that partial refolding of the A subunit occurs during the Western blot process, as we observed for monoclonal antibody 13C4 in another study (Smith et al. (2006) *Infect. Immun.* 74:6992-6998).

The sequences of the three surface loops that form the 11E10 monoclonal antibody neutralizing epitope on Stx2 are conserved among the Stx2 variants. There are a few amino acids that differ within those regions in Stx2d and Stx2e, two toxins that are rarely found in human isolates (Melton-Celsa et al. (2005), supra). However, the 11E10 monoclonal antibody did detect and partially neutralize the cytotoxic activity of Stx2 and all of the Stx2 variants analyzed in this report (Stx2c, Stx2d, Stx2d$_{act}$, and Stx2e). The finding that Stx2e is neutralized by 11E10 on Vero cells but recognized poorly in the Western format as compared to Stx2 may indicate that the sequences in region B that are different between Stx2 and Stx2e are more important for recognition on Western blot than for neutralization. However, the fact that 11E10 has the capacity to neutralize all of these variant toxins suggests that it may be a good candidate for treating disease mediated by Stx2 and Stx2-related toxins in humans. Indeed, we have found that 11E10 is protective in a toxemia (Stx2) model of disease (Sauter et al. (2008) *Infect. Immun.* 76:4469-4478) and an orally-fed mouse model of disease with a strain that produces Stx2d$_{act}$ (Edwards et al., supra). We are currently involved in an on-going laboratory evaluation of the humanized version of 11E10, cαStx2, on which Phase I safety testing has been completed (Dowling et al., supra).

We attempted to protect mice from Stx2 challenge by immunization with the toxoided chimeric Stx1 molecule that contained just the 29 amino acids from Stx2 that comprise the 11E10 epitope. We found that although the immunized mice raised a protective response to Stx1, only a few of the mice generated Stx2-neutralizing antibodies, and these were of low titer. The response to Stx2 may have been improved with additional boosts of the chimeric toxoid.

We found that 11E10 blocked the enzymatic activity of Stx2 in vitro, a fact that we predicted based on the close proximity of the 11E10 epitope to the toxin active site. We further observed that 11E10 altered the overall distribution of the toxin inside the cell, a finding that is similar to the data on Stx2 neutralization by a different StxA2 monoclonal antibody, 5C12, as reported by Krautz-Peterson et al. ((2008) *Infect. Immun.* 76:1931-1939). These investigators concluded that when monoclonal antibody 5C12 binds StxA2 it alters the intracellular trafficking pattern of the toxin (Krautz-Peterson et al, supra). Our data indicate that once the 11E10/Stx2 complex binds to and enters the host cell, the antibody may prevent toxin trafficking to the target ribosomes in the cytosol. However, since we demonstrated that 11E10 prevented the enzymatic function of the toxin in vitro, we predict that should the A subunit of Stx2 complexed with 11E10 reach its enzymatic target in the cytosol, the toxin would be unable to kill the cell.

OTHER EMBODIMENTS

Various modifications and variations of the described methods and compositions of the invention will be apparent to those skilled in the art without departing from the scope and spirit of the invention. Although the invention has been described in connection with specific desired embodiments, it should be understood that the invention as claimed should not be unduly limited to such specific embodiments.

All patents, patent applications, and publications mentioned in this specification are herein incorporated by reference to the same extent as if each independent publication was specifically and individually incorporated by reference.

What is claimed is:

1. A composition for stimulating an immune response against Stx2 comprising a pharmaceutically acceptable carrier and at least one purified polypeptide, said polypeptide consisting of SEQ ID NO: 1, SEQ ID NO:2, or SEQ ID NO:3 and a non-Stx2 protein scaffold, wherein said SEQ ID NO: 1, SEQ ID NO: 2, or SEQ ID NO: 3 is inserted into said non-Stx2 protein scaffold, wherein the amino acid sequence of said non-Stx2 protein scaffold shares at least 75% sequence identity with the amino acid sequence of Stx1 subunit A, and wherein said polypeptide has the antigenicity of Stx2.

2. The composition of claim 1, wherein said scaffold shares at least 80% identity to Stx1 subunit A.

3. The composition of claim 1, wherein said composition further comprises an adjuvant.

4. A purified polypeptide consisting of:
SEQ ID NO: 1, SEQ ID NO: 2, or SEQ ID NO: 3 and a non-Stx2 protein scaffold, wherein said SEQ ID NO: 1, SEQ ID NO: 2, or SEQ ID NO: 3 is inserted into said non-Stx2 protein scaffold, wherein the amino acid sequence of said non-Stx2 protein scaffold shares at least 75% sequence identity with the amino acid sequence of Stx1 subunit A, and wherein said polypeptide has the antigenicity of Stx2.

5. The purified polypeptide of claim 4, wherein said scaffold shares at least 80% identity to Stx1 subunit A.

6. A composition for stimulating an immune response against Stx2 comprising a pharmaceutically acceptable carrier and at least one purified polypeptide, said polypeptide consisting of:
(i) SEQ ID NO: 1, SEQ ID NO:2, or SEQ ID NO:3; and
(ii) a non-Stx2 protein scaffold, wherein said SEQ ID NO: 1, SEQ ID NO:2, or SEQ ID NO:3 is inserted into said non-Stx2 protein scaffold wherein said polypeptide does not include full-length Stx2 polypeptide.

* * * * *

SEQUENCE LISTING

<160> NUMBER OF SEQ ID NOS: 55

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1

Asn His Thr Pro Pro Gly Ser Tyr
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Construct

<400> SEQUENCE: 2

Thr His Ile Ser Val
1               5

<210> SEQ ID NO 3
<211> LENGTH: 16
<212> TYPE: PRT
<213> ORGANISM: Artificial Sequence
<220> FEATURE:
<223> OTHER INFORMATION: Synthetic Construct

<400> SEQUENCE: 3

Gln Gly Ala Arg Ser Val Arg Ala Val Asn Glu Glu Ser Gln Pro Glu
1               5                   10                  15

<210> SEQ ID NO 4
<211> LENGTH: 315
<212> TYPE: PRT
<213> ORGANISM: Artificial Sequence
<220> FEATURE:
<223> OTHER INFORMATION: Synthetic Construct

<400> SEQUENCE: 4

Met Lys Ile Ile Ile Phe Arg Val Leu Thr Phe Phe Phe Val Ile Phe
1               5                   10                  15

Ser Val Asn Val Val Ala Lys Glu Phe Thr Leu Asp Phe Ser Thr Ala
                20                  25                  30

Lys Thr Tyr Val Asp Ser Leu Asn Val Ile Arg Ser Ala Ile Gly Thr
            35                  40                  45

Pro Leu Gln Thr Ile Ser Ser Gly Gly Thr Ser Leu Leu Met Ile Asn
        50                  55                  60

His Thr Pro Pro Gly Ser Tyr Phe Ala Val Asp Val Arg Gly Ile Asp
65                  70                  75                  80

Pro Glu Glu Gly Arg Phe Asn Asn Leu Arg Leu Ile Val Glu Arg Asn
                85                  90                  95

Asn Leu Tyr Val Thr Gly Phe Val Asn Arg Thr Asn Asn Val Phe Tyr
                100                 105                 110

Arg Phe Ala Asp Phe Ser His Val Thr Phe Pro Gly Thr Thr Ala Val
            115                 120                 125

Thr Leu Ser Gly Asp Ser Ser Tyr Thr Thr Leu Gln Arg Val Ala Gly
        130                 135                 140

Ile Ser Arg Thr Gly Met Gln Ile Asn Arg His Ser Leu Thr Thr Ser

```
145             150             155             160
Tyr Leu Asp Leu Met Ser His Ser Gly Thr Ser Leu Thr Gln Ser Val
                165             170             175

Ala Arg Ala Met Leu Arg Phe Val Thr Val Thr Ala Glu Ala Leu Arg
            180             185             190

Phe Arg Gln Ile Gln Arg Gly Phe Arg Thr Thr Leu Asp Asp Leu Ser
        195             200             205

Gly Arg Ser Tyr Val Met Thr Ala Glu Asp Val Asp Leu Thr Leu Asn
    210             215             220

Trp Gly Arg Leu Ser Ser Val Leu Pro Asp Tyr His Gly Gln Asp Ser
225             230             235             240

Val Arg Val Gly Arg Ile Ser Phe Gly Ser Ile Asn Ala Ile Leu Gly
                245             250             255

Ser Val Ala Leu Ile Leu Asn Cys His His Ala Ser Arg Val Ala
            260             265             270

Arg Met Ala Ser Asp Glu Phe Pro Ser Met Cys Pro Ala Asp Gly Arg
        275             280             285

Val Arg Gly Ile Thr His Asn Lys Ile Leu Trp Asp Ser Ser Thr Leu
    290             295             300

Gly Ala Ile Leu Met Arg Arg Thr Ile Ser Ser
305             310             315

<210> SEQ ID NO 5
<211> LENGTH: 315
<212> TYPE: PRT
<213> ORGANISM: Artificial Sequence
<220> FEATURE:
<223> OTHER INFORMATION: Synthetic Construct

<400> SEQUENCE: 5

Met Lys Ile Ile Ile Phe Arg Val Leu Thr Phe Phe Phe Val Ile Phe
1               5               10              15

Ser Val Asn Val Val Ala Lys Glu Phe Thr Leu Asp Phe Ser Thr Ala
            20              25              30

Lys Thr Tyr Val Asp Ser Leu Asn Val Ile Arg Ser Ala Ile Gly Thr
        35              40              45

Pro Leu Gln Thr Ile Ser Ser Gly Gly Thr Ser Leu Leu Met Ile Asn
    50              55              60

His Thr Pro Pro Gly Ser Tyr Phe Ala Val Asp Val Arg Gly Ile Asp
65              70              75              80

Pro Glu Glu Gly Arg Phe Asn Asn Leu Arg Leu Ile Val Glu Arg Asn
                85              90              95

Asn Leu Tyr Val Thr Gly Phe Val Asn Arg Thr Asn Asn Val Phe Tyr
            100             105             110

Arg Phe Ala Asp Phe Thr His Ile Ser Val Pro Gly Thr Thr Ala Val
        115             120             125

Thr Leu Ser Gly Asp Ser Ser Tyr Thr Thr Leu Gln Arg Val Ala Gly
    130             135             140

Ile Ser Arg Thr Gly Met Gln Ile Asn Arg His Ser Leu Thr Thr Ser
145             150             155             160

Tyr Leu Asp Leu Met Ser His Ser Gly Thr Ser Leu Thr Gln Ser Val
                165             170             175

Ala Arg Ala Met Leu Arg Phe Val Thr Val Thr Ala Glu Ala Leu Arg
            180             185             190

Phe Arg Gln Ile Gln Arg Gly Phe Arg Thr Thr Leu Asp Asp Leu Ser
```

195                 200                 205
Gly Arg Ser Tyr Val Met Thr Ala Glu Asp Val Asp Leu Thr Leu Asn
        210                 215                 220
Trp Gly Arg Leu Ser Ser Val Leu Pro Asp Tyr His Gly Gln Asp Ser
225                 230                 235                 240
Val Arg Val Gly Arg Ile Ser Phe Gly Ser Ile Asn Ala Ile Leu Gly
                245                 250                 255
Ser Val Ala Leu Ile Leu Asn Cys His His Ala Ser Arg Val Ala
            260                 265                 270
Arg Met Ala Ser Asp Glu Phe Pro Ser Met Cys Pro Ala Asp Gly Arg
            275                 280                 285
Val Arg Gly Ile Thr His Asn Lys Ile Leu Trp Asp Ser Ser Thr Leu
        290                 295                 300
Gly Ala Ile Leu Met Arg Arg Thr Ile Ser Ser
305                 310                 315

<210> SEQ ID NO 6
<211> LENGTH: 315
<212> TYPE: PRT
<213> ORGANISM: Artificial Sequence
<220> FEATURE:
<223> OTHER INFORMATION: Synthetic Construct

<400> SEQUENCE: 6

Met Lys Ile Ile Ile Phe Arg Val Leu Thr Phe Phe Phe Val Ile Phe
1               5                   10                  15
Ser Val Asn Val Val Ala Lys Glu Phe Thr Leu Asp Phe Ser Thr Ala
            20                  25                  30
Lys Thr Tyr Val Asp Ser Leu Asn Val Ile Arg Ser Ala Ile Gly Thr
        35                  40                  45
Pro Leu Gln Thr Ile Ser Ser Gly Gly Thr Ser Leu Leu Met Ile Asn
    50                  55                  60
His Thr Pro Pro Gly Ser Tyr Phe Ala Val Asp Val Arg Gly Ile Asp
65                  70                  75                  80
Pro Glu Glu Gly Arg Phe Asn Asn Leu Arg Leu Ile Val Glu Arg Asn
                85                  90                  95
Asn Leu Tyr Val Thr Gly Phe Val Asn Arg Thr Asn Asn Val Phe Tyr
            100                 105                 110
Arg Phe Ala Asp Phe Ser His Val Thr Phe Pro Gly Thr Thr Ala Val
        115                 120                 125
Thr Leu Ser Gly Asp Ser Ser Tyr Thr Thr Leu Gln Arg Val Ala Gly
    130                 135                 140
Ile Ser Arg Thr Gly Met Gln Ile Asn Arg His Ser Leu Thr Thr Ser
145                 150                 155                 160
Tyr Leu Asp Leu Met Ser His Ser Gly Thr Ser Leu Thr Gln Ser Val
                165                 170                 175
Ala Arg Ala Met Leu Arg Phe Val Thr Val Thr Ala Glu Ala Leu Arg
            180                 185                 190
Phe Arg Gln Ile Gln Arg Gly Phe Arg Thr Thr Leu Asp Asp Leu Ser
        195                 200                 205
Gly Arg Ser Tyr Val Met Thr Ala Glu Asp Val Asp Leu Thr Leu Asn
            210                 215                 220
Trp Gly Arg Leu Ser Ser Val Leu Pro Asp Tyr His Gly Gln Asp Ser
225                 230                 235                 240
Val Arg Val Gly Arg Ile Ser Phe Gly Ser Ile Asn Ala Ile Leu Gly

```
                        245                 250                 255
Ser Val Ala Leu Ile Leu Asn Cys His His Gln Gly Ala Arg Ser Val
            260                 265                 270

Arg Ala Val Asn Glu Glu Ser Gln Pro Glu Cys Pro Ala Asp Gly Arg
        275                 280                 285

Val Arg Gly Ile Thr His Asn Lys Ile Leu Trp Asp Ser Ser Thr Leu
    290                 295                 300

Gly Ala Ile Leu Met Arg Arg Thr Ile Ser Ser
305                 310                 315

<210> SEQ ID NO 7
<211> LENGTH: 315
<212> TYPE: PRT
<213> ORGANISM: Artificial Sequence
<220> FEATURE:
<223> OTHER INFORMATION: Synthetic Construct

<400> SEQUENCE: 7

Met Lys Ile Ile Ile Phe Arg Val Leu Thr Phe Phe Phe Val Ile Phe
1               5                   10                  15

Ser Val Asn Val Val Ala Lys Glu Phe Thr Leu Asp Phe Ser Thr Ala
            20                  25                  30

Lys Thr Tyr Val Asp Ser Leu Asn Val Ile Arg Ser Ala Ile Gly Thr
        35                  40                  45

Pro Leu Gln Thr Ile Ser Ser Gly Gly Thr Ser Leu Leu Met Ile Asp
    50                  55                  60

Ser Gly Ser Gly Asp Asn Leu Phe Ala Val Asp Val Arg Gly Ile Asp
65                  70                  75                  80

Pro Glu Glu Gly Arg Phe Asn Asn Leu Arg Leu Ile Val Glu Arg Asn
                85                  90                  95

Asn Leu Tyr Val Thr Gly Phe Val Asn Arg Thr Asn Asn Val Phe Tyr
            100                 105                 110

Arg Phe Ala Asp Phe Thr His Ile Ser Val Pro Gly Thr Thr Ala Val
        115                 120                 125

Thr Leu Ser Gly Asp Ser Ser Tyr Thr Thr Leu Gln Arg Val Ala Gly
    130                 135                 140

Ile Ser Arg Thr Gly Met Gln Ile Asn Arg His Ser Leu Thr Thr Ser
145                 150                 155                 160

Tyr Leu Asp Leu Met Ser His Ser Gly Thr Ser Leu Thr Gln Ser Val
                165                 170                 175

Ala Arg Ala Met Leu Arg Phe Val Thr Val Thr Ala Glu Ala Leu Arg
            180                 185                 190

Phe Arg Gln Ile Gln Arg Gly Phe Arg Thr Thr Leu Asp Asp Leu Ser
        195                 200                 205

Gly Arg Ser Tyr Val Met Thr Ala Glu Asp Val Asp Leu Thr Leu Asn
    210                 215                 220

Trp Gly Arg Leu Ser Ser Val Leu Pro Asp Tyr His Gly Gln Asp Ser
225                 230                 235                 240

Val Arg Val Gly Arg Ile Ser Phe Gly Ser Ile Asn Ala Ile Leu Gly
                245                 250                 255

Ser Val Ala Leu Ile Leu Asn Cys His His Gln Gly Ala Arg Ser Val
            260                 265                 270

Arg Ala Val Asn Glu Glu Ser Gln Pro Glu Cys Pro Ala Asp Gly Arg
        275                 280                 285

Val Arg Gly Ile Thr His Asn Lys Ile Leu Trp Asp Ser Ser Thr Leu
```

```
                290                 295                 300
Gly Ala Ile Leu Met Arg Arg Thr Ile Ser Ser
305                 310                 315

<210> SEQ ID NO 8
<211> LENGTH: 315
<212> TYPE: PRT
<213> ORGANISM: Artificial Sequence
<220> FEATURE:
<223> OTHER INFORMATION: Synthetic Construct

<400> SEQUENCE: 8

Met Lys Ile Ile Ile Phe Arg Val Leu Thr Phe Phe Val Ile Phe
1               5                   10                  15

Ser Val Asn Val Val Ala Lys Glu Phe Thr Leu Asp Phe Ser Thr Ala
                20                  25                  30

Lys Thr Tyr Val Asp Ser Leu Asn Val Ile Arg Ser Ala Ile Gly Thr
            35                  40                  45

Pro Leu Gln Thr Ile Ser Ser Gly Gly Thr Ser Leu Leu Met Ile Asn
        50                  55                  60

His Thr Pro Pro Gly Ser Tyr Phe Ala Val Asp Val Arg Gly Ile Asp
65                  70                  75                  80

Pro Glu Glu Gly Arg Phe Asn Asn Leu Arg Leu Ile Val Glu Arg Asn
                85                  90                  95

Asn Leu Tyr Val Thr Gly Phe Val Asn Arg Thr Asn Asn Val Phe Tyr
            100                 105                 110

Arg Phe Ala Asp Phe Thr His Ile Ser Val Pro Gly Thr Thr Ala Val
        115                 120                 125

Thr Leu Ser Gly Asp Ser Ser Tyr Thr Thr Leu Gln Arg Val Ala Gly
    130                 135                 140

Ile Ser Arg Thr Gly Met Gln Ile Asn Arg His Ser Leu Thr Thr Ser
145                 150                 155                 160

Tyr Leu Asp Leu Met Ser His Ser Gly Thr Ser Leu Thr Gln Ser Val
                165                 170                 175

Ala Arg Ala Met Leu Arg Phe Val Thr Val Thr Ala Glu Ala Leu Arg
            180                 185                 190

Phe Arg Gln Ile Gln Arg Gly Phe Arg Thr Thr Leu Asp Asp Leu Ser
        195                 200                 205

Gly Arg Ser Tyr Val Met Thr Ala Glu Asp Val Asp Leu Thr Leu Asn
    210                 215                 220

Trp Gly Arg Leu Ser Ser Val Leu Pro Asp Tyr His Gly Gln Asp Ser
225                 230                 235                 240

Val Arg Val Gly Arg Ile Ser Phe Gly Ser Ile Asn Ala Ile Leu Gly
                245                 250                 255

Ser Val Ala Leu Ile Leu Asn Cys His His Gln Gly Ala Arg Ser Val
            260                 265                 270

Arg Ala Val Asn Glu Glu Ser Gln Pro Glu Cys Pro Ala Asp Gly Arg
        275                 280                 285

Val Arg Gly Ile Thr His Asn Lys Ile Leu Trp Asp Ser Ser Thr Leu
    290                 295                 300

Gly Ala Ile Leu Met Arg Arg Thr Ile Ser Ser
305                 310                 315

<210> SEQ ID NO 9
<211> LENGTH: 1227
<212> TYPE: DNA
```

<213> ORGANISM: Escherichia coli

<400> SEQUENCE: 9

| | | | | | |
|---|---|---|---|---|---|
| atgaaaataa | ttatttttag | agtgctaact | tttttctttg | ttatcttttc | agttaatgtg | 60 |
| gtggcgaagg | aatttacctt | agacttctcg | actgcaaaga | cgtatgtaga | ttcgctgaat | 120 |
| gtcattcgct | ctgcaatagg | tactccatta | cagactattt | catcaggagg | tacgtcttta | 180 |
| ctgatgattg | atagtggctc | agggataat | ttgtttgcag | ttgatgtcag | agggatagat | 240 |
| ccagaggaag | ggcggtttaa | taatctacgg | cttattgttg | aacgaaataa | tttatatgtg | 300 |
| acaggatttg | ttaacaggac | aaataatgtt | tttatcgct | ttgctgattt | ttcacatgtt | 360 |
| acctttccag | gtacaacagc | ggttacattg | tctggtgaca | gtagctatac | cacgttacag | 420 |
| cgtgttgcag | ggatcagtcg | tacggggatg | cagataaatc | gccattcgtt | gactacttct | 480 |
| tatctggatt | taatgtcgca | tagtggaacc | tcactgacgc | agtctgtggc | aagagcgatg | 540 |
| ttacggtttg | ttactgtgac | agctgaagct | ttacgttttc | ggcaaataca | gaggggattt | 600 |
| cgtacaacac | tggatgatct | cagtgggcgt | tcttatgtaa | tgactgctga | agatgttgat | 660 |
| cttacattga | actggggaag | gttgagtagc | gtcctgcctg | actatcatgg | acaagactct | 720 |
| gttcgtgtag | gaagaatttc | ttttggaagc | attaatgcaa | ttctgggaag | cgtggcatta | 780 |
| atactgaatt | gtcatcatca | tgcatcgcga | gttgccagaa | tggcatctga | tgagtttcct | 840 |
| tctatgtgtc | cggcagatgg | aagagtccgt | gggattacgc | acaataaaat | attgtgggat | 900 |
| tcatccactc | tgggggcaat | tctgatgcgc | agaactatta | gcagttgagg | gggtaaaatg | 960 |
| aaaaaaacat | tattaatagc | tgcatcgctt | tcatttttt | cagcaagtgc | gctggcgacg | 1020 |
| cctgattgtg | taactggaaa | ggtggagtat | acaaaatata | atgatgacga | tacctttaca | 1080 |
| gttaaagtgg | gtgataaaga | attatttacc | aacagatgga | atcttcagtc | tcttcttctc | 1140 |
| agtgcgcaaa | ttacggggat | gactgtaacc | attaaaacta | tgcctgtca | taatggaggg | 1200 |
| ggattcagcg | aagttatttt | tcgttga | | | | 1227 |

<210> SEQ ID NO 10
<211> LENGTH: 948
<212> TYPE: DNA
<213> ORGANISM: Escherichia coli

<400> SEQUENCE: 10

| | | | | | |
|---|---|---|---|---|---|
| atgaaaataa | ttatttttag | agtgctaact | tttttctttg | ttatcttttc | agttaatgtg | 60 |
| gtggcgaagg | aatttacctt | agacttctcg | actgcaaaga | cgtatgtaga | ttcgctgaat | 120 |
| gtcattcgct | ctgcaatagg | tactccatta | cagactattt | catcaggagg | tacgtcttta | 180 |
| ctgatgattg | atagtggctc | agggataat | ttgtttgcag | ttgatgtcag | agggatagat | 240 |
| ccagaggaag | ggcggtttaa | taatctacgg | cttattgttg | aacgaaataa | tttatatgtg | 300 |
| acaggatttg | ttaacaggac | aaataatgtt | tttatcgct | ttgctgattt | ttcacatgtt | 360 |
| acctttccag | gtacaacagc | ggttacattg | tctggtgaca | gtagctatac | cacgttacag | 420 |
| cgtgttgcag | ggatcagtcg | tacggggatg | cagataaatc | gccattcgtt | gactacttct | 480 |
| tatctggatt | taatgtcgca | tagtggaacc | tcactgacgc | agtctgtggc | aagagcgatg | 540 |
| ttacggtttg | ttactgtgac | agctgaagct | ttacgttttc | ggcaaataca | gaggggattt | 600 |
| cgtacaacac | tggatgatct | cagtgggcgt | tcttatgtaa | tgactgctga | agatgttgat | 660 |
| cttacattga | actggggaag | gttgagtagc | gtcctgcctg | actatcatgg | acaagactct | 720 |
| gttcgtgtag | gaagaatttc | ttttggaagc | attaatgcaa | ttctgggaag | cgtggcatta | 780 |

```
atactgaatt gtcatcatca tgcatcgcga gttgccagaa tggcatctga tgagtttcct      840
tctatgtgtc cggcagatgg aagagtccgt gggattacgc acaataaaat attgtgggat      900
tcatccactc tgggggcaat tctgatgcgc agaactatta gcagttga                    948
```

<210> SEQ ID NO 11
<211> LENGTH: 270
<212> TYPE: DNA
<213> ORGANISM: Escherichia coli

<400> SEQUENCE: 11

```
atgaaaaaaa cattattaat agctgcatcg ctttcatttt tttcagcaag tgcgctggcg       60
acgcctgatt gtgtaactgg aaaggtggag tatacaaaat ataatgatga cgatacccttt    120 acagttaaag tgggtgataa agaattattt accaacagat ggaatcttca gtctcttctt     180
ctcagtgcgc aaattacggg gatgactgta accattaaaa ctaatgcctg tcataatgga     240
gggggattca gcgaagttat ttttcgttga                                        270
```

<210> SEQ ID NO 12
<211> LENGTH: 315
<212> TYPE: PRT
<213> ORGANISM: Escherichia coli

<400> SEQUENCE: 12

```
Met Lys Ile Ile Ile Phe Arg Val Leu Thr Phe Phe Phe Val Ile Phe
1               5                   10                  15

Ser Val Asn Val Val Ala Lys Glu Phe Thr Leu Asp Phe Ser Thr Ala
            20                  25                  30

Lys Thr Tyr Val Asp Ser Leu Asn Val Ile Arg Ser Ala Ile Gly Thr
        35                  40                  45

Pro Leu Gln Thr Ile Ser Ser Gly Gly Thr Ser Leu Leu Met Ile Asp
    50                  55                  60

Ser Gly Ser Gly Asp Asn Leu Phe Ala Val Asp Val Arg Gly Ile Asp
65                  70                  75                  80

Pro Glu Glu Gly Arg Phe Asn Asn Leu Arg Leu Ile Val Glu Arg Asn
                85                  90                  95

Asn Leu Tyr Val Thr Gly Phe Val Asn Arg Thr Asn Asn Val Phe Tyr
            100                 105                 110

Arg Phe Ala Asp Phe Ser His Val Thr Phe Pro Gly Thr Thr Ala Val
        115                 120                 125

Thr Leu Ser Gly Asp Ser Ser Tyr Thr Thr Leu Gln Arg Val Ala Gly
    130                 135                 140

Ile Ser Arg Thr Gly Met Gln Ile Asn Arg His Ser Leu Thr Thr Ser
145                 150                 155                 160

Tyr Leu Asp Leu Met Ser His Ser Gly Thr Ser Leu Thr Gln Ser Val
                165                 170                 175

Ala Arg Ala Met Leu Arg Phe Val Thr Val Thr Ala Glu Ala Leu Arg
            180                 185                 190

Phe Arg Gln Ile Gln Arg Gly Phe Arg Thr Thr Leu Asp Asp Leu Ser
        195                 200                 205

Gly Arg Ser Tyr Val Met Thr Ala Glu Asp Val Asp Leu Thr Leu Asn
    210                 215                 220

Trp Gly Arg Leu Ser Ser Val Leu Pro Asp Tyr His Gly Gln Asp Ser
225                 230                 235                 240

Val Arg Val Gly Arg Ile Ser Phe Gly Ser Ile Asn Ala Ile Leu Gly
```

```
            245                 250                 255
Ser Val Ala Leu Ile Leu Asn Cys His His Ala Ser Arg Val Ala
        260                 265                 270

Arg Met Ala Ser Asp Glu Phe Pro Ser Met Cys Pro Ala Asp Gly Arg
        275                 280                 285

Val Arg Gly Ile Thr His Asn Lys Ile Leu Trp Asp Ser Ser Thr Leu
290                 295                 300

Gly Ala Ile Leu Met Arg Arg Thr Ile Ser Ser
305                 310                 315

<210> SEQ ID NO 13
<211> LENGTH: 89
<212> TYPE: PRT
<213> ORGANISM: Escherichia coli

<400> SEQUENCE: 13

Met Lys Lys Thr Leu Leu Ile Ala Ala Ser Leu Ser Phe Phe Ser Ala
1               5                   10                  15

Ser Ala Leu Ala Thr Pro Asp Cys Val Thr Gly Lys Val Glu Tyr Thr
            20                  25                  30

Lys Tyr Asn Asp Asp Asp Thr Phe Thr Val Lys Val Gly Asp Lys Glu
        35                  40                  45

Leu Phe Thr Asn Arg Trp Asn Leu Gln Ser Leu Leu Leu Ser Ala Gln
    50                  55                  60

Ile Thr Gly Met Thr Val Thr Ile Lys Thr Asn Ala Cys His Asn Gly
65                  70                  75                  80

Gly Gly Phe Ser Glu Val Ile Phe Arg
                85

<210> SEQ ID NO 14
<211> LENGTH: 1241
<212> TYPE: DNA
<213> ORGANISM: Escherichia coli

<400> SEQUENCE: 14
atgaagtgta tattatttaa atgggtactg tgcctgttac tgggttttc ttcggtatcc      60 tattcccggg agtttacgat agacttttcg acccaacaaa gttatgtctc ttcgttaaat     120
agtatacgga cagagatatc gaccctctt gaacatatat ctcaggggac acatcggtg      180 tctgttatta accacacccc accgggcagt tatttgctg tggatatacg agggcttgat     240
gtctatcagg gcgttttga ccatcttcgt ctgattattg agcaaaataa tttatatgtg     300
gccgggttcg ttaatacggc aacaaatact ttctaccgtt tttcagattt tacacatata     360
tcagtgcccg gtgtgacaac ggtttccatg acaacggaca gcagttatac cactctgcaa     420
cgtgtcgcag cgctggaacg ttccggaatg caaatcagtc gtcactcact ggtttcatca     480
tatctggcgt taatggagtt cagtggtaat acaatgacca gagatgcatc cagagcagtt     540
ctgcgttttg tcactgtcac agcagaagcc ttacgcttca ggcagataca gagagaattt     600
cgtcaggcac tgtctgaaac tgctcctgtg tatacgatga cgccgggaga cgtggacctc     660
actctgaact gggggcgaat cagcaatgtg cttccggagt atcggggaga ggatggtgtc     720
agagtgggga gaatatcctt taataatata tcagcgatac tggggactgt ggccgttata     780
ctgaattgcc atcatcaggg ggcgcgttct gttcgcgccg tgaatgaaga gagtcaacca     840
gaatgtcaga taactggcga caggcctgtt ataaaaataa acaatacatt atgggaaagt     900
aatacagctg cagcgtttct gaacagaaag tcacagtttt tatatacaac gggtaaataa     960
```

```
aggagttaag catgaagaag atgtttatgg cggtttat  tgcattagct tctgttaatg    1020
caatggcggc ggattgtgct aaaggtaaaa ttgagttttc aagtataat gaggatgaca    1080 catttacagt gaaggttgac gggaaagaat actggaccag tcgctggaat ctgcaaccgt   1140
tactgcaaag tgctcagttg acaggaatga ctgtcacaat caaatccagt acctgtgaat   1200
caggctccgg atttgctgaa gtgcagttta ataatgactg a                       1241
```

<210> SEQ ID NO 15
<211> LENGTH: 960
<212> TYPE: DNA
<213> ORGANISM: Escherichia coli

<400> SEQUENCE: 15

```
atgaagtgta tattatttaa atgggtactg tgcctgttac tgggttttc  ttcggtatcc     60 tattcccggg agtttacgat agacttttcg acccaacaaa gttatgtctc ttcgttaaat    120
agtatacgga cagagatatc gaccccctctt gaacatatat ctcaggggac acatcggtg    180 tctgttatta accacacccc accgggcagt tattttgctg tggatatacg agggcttgat    240
gtctatcagg cgcgttttga ccatcttcgt ctgattattg agcaaaataa tttatatgtg    300
gccgggttcg ttaatacggc aacaaatact ttctaccgtt tttcagattt tacacatata    360
tcagtgcccg gtgtgacaac ggtttccatg acaacggaca gcagttatac cactctgcaa    420
cgtgtcgcag cgctggaacg ttccggaatg caaatcagtc gtcactcact ggtttcatca    480
tatctggcgt taatggagtt cagtggtaat acaatgacca gagatgcatc cagagcagtt    540
ctgcgttttg tcactgtcac agcagaagcc ttacgcttca ggcagataca gagagaattt    600
cgtcaggcac tgtctgaaac tgctcctgtg tatacgatga cgccgggaga cgtggacctc    660
actctgaact gggggcgaat cagcaatgtg cttccggagt atcggggaga ggatggtgtc    720
agagtgggga gaatatcctt taataatata tcagcgatac tggggactgt ggccgttata    780
ctgaattgcc atcatcaggg ggcgcgttct gttcgcgccg tgaatgaaga gagtcaacca    840
gaatgtcaga taactggcga caggcctgtt ataaaaataa acaatacatt atgggaaagt    900
aatacagctg cagcgtttct gaacagaaag tcacagtttt tatatacaac gggtaaataa    960
```

<210> SEQ ID NO 16
<211> LENGTH: 270
<212> TYPE: DNA
<213> ORGANISM: Escherichia coli

<400> SEQUENCE: 16

```
atgaagaaga tgtttatggc ggttttattt gcattagctt ctgttaatgc aatggcggcg     60
gattgtgcta aaggtaaaat tgagttttcc aagtataatg aggatgacac atttacagtg    120
aaggttgacg ggaaagaata ctggaccagt cgctggaatc tgcaaccgtt actgcaaagt    180
gctcagttga caggaatgac tgtcacaatc aaatccagta cctgtgaatc aggctccgga    240
tttgctgaag tgcagtttaa taatgactga                                      270
```

<210> SEQ ID NO 17
<211> LENGTH: 319
<212> TYPE: PRT
<213> ORGANISM: Escherichia coli

<400> SEQUENCE: 17

```
Met Lys Cys Ile Leu Phe Lys Trp Val Leu Cys Leu Leu Leu Gly Phe
1               5                   10                  15
```

Ser Ser Val Ser Tyr Ser Arg Glu Phe Thr Ile Asp Phe Ser Thr Gln
            20                  25                  30

Gln Ser Tyr Val Ser Ser Leu Asn Ser Ile Arg Thr Glu Ile Ser Thr
        35                  40                  45

Pro Leu Glu His Ile Ser Gln Gly Thr Thr Ser Val Ser Val Ile Asn
50                  55                  60

His Thr Pro Pro Gly Ser Tyr Phe Ala Val Asp Ile Arg Gly Leu Asp
65                  70                  75                  80

Val Tyr Gln Ala Arg Phe Asp His Leu Arg Leu Ile Ile Glu Gln Asn
                85                  90                  95

Asn Leu Tyr Val Ala Gly Phe Val Asn Thr Ala Thr Asn Thr Phe Tyr
            100                 105                 110

Arg Phe Ser Asp Phe Thr His Ile Ser Val Pro Gly Val Thr Thr Val
        115                 120                 125

Ser Met Thr Thr Asp Ser Ser Tyr Thr Thr Leu Gln Arg Val Ala Ala
    130                 135                 140

Leu Glu Arg Ser Gly Met Gln Ile Ser Arg His Ser Leu Val Ser Ser
145                 150                 155                 160

Tyr Leu Ala Leu Met Glu Phe Ser Gly Asn Thr Met Thr Arg Asp Ala
                165                 170                 175

Ser Arg Ala Val Leu Arg Phe Val Thr Val Thr Ala Glu Ala Leu Arg
            180                 185                 190

Phe Arg Gln Ile Gln Arg Glu Phe Arg Gln Ala Leu Ser Glu Thr Ala
        195                 200                 205

Pro Val Tyr Thr Met Thr Pro Gly Asp Val Asp Leu Thr Leu Asn Trp
    210                 215                 220

Gly Arg Ile Ser Asn Val Leu Pro Glu Tyr Arg Gly Glu Asp Gly Val
225                 230                 235                 240

Arg Val Gly Arg Ile Ser Phe Asn Asn Ile Ser Ala Ile Leu Gly Thr
                245                 250                 255

Val Ala Val Ile Leu Asn Cys His His Gln Gly Ala Arg Ser Val Arg
            260                 265                 270

Ala Val Asn Glu Glu Ser Gln Pro Glu Cys Gln Ile Thr Gly Asp Arg
        275                 280                 285

Pro Val Ile Lys Ile Asn Asn Thr Leu Trp Glu Ser Asn Thr Ala Ala
    290                 295                 300

Ala Phe Leu Asn Arg Lys Ser Gln Phe Leu Tyr Thr Thr Gly Lys
305                 310                 315

<210> SEQ ID NO 18
<211> LENGTH: 89
<212> TYPE: PRT
<213> ORGANISM: Escherichia coli

<400> SEQUENCE: 18

Met Lys Lys Met Phe Met Ala Val Leu Phe Ala Leu Ala Ser Val Asn
1               5                   10                  15

Ala Met Ala Ala Asp Cys Ala Lys Gly Lys Ile Glu Phe Ser Lys Tyr
            20                  25                  30

Asn Glu Asp Asp Thr Phe Thr Val Lys Val Asp Gly Lys Glu Tyr Trp
        35                  40                  45

Thr Ser Arg Trp Asn Leu Gln Pro Leu Leu Gln Ser Ala Gln Leu Thr
    50                  55                  60

Gly Met Thr Val Thr Ile Lys Ser Ser Thr Cys Glu Ser Gly Ser Gly

Phe Ala Glu Val Gln Phe Asn Asn Asp
            85

<210> SEQ ID NO 19
<211> LENGTH: 5
<212> TYPE: PRT
<213> ORGANISM: Artificial Sequence
<220> FEATURE:
<223> OTHER INFORMATION: Synthetic Construct

<400> SEQUENCE: 19

Ala His Ile Ser Leu
1               5

<210> SEQ ID NO 20
<211> LENGTH: 17
<212> TYPE: DNA
<213> ORGANISM: Artificial Sequence
<220> FEATURE:
<223> OTHER INFORMATION: Synthetic Construct

<400> SEQUENCE: 20
taaggaggac agctatg                                                    17

<210> SEQ ID NO 21
<211> LENGTH: 36
<212> TYPE: DNA
<213> ORGANISM: Artificial Sequence
<220> FEATURE:
<223> OTHER INFORMATION: Synthetic Construct

<400> SEQUENCE: 21
gatcggatcc ccctgtaacg aagtttgcgt aacagc                               36

<210> SEQ ID NO 22
<211> LENGTH: 39
<212> TYPE: DNA
<213> ORGANISM: Artificial Sequence
<220> FEATURE:
<223> OTHER INFORMATION: Synthetic Construct

<400> SEQUENCE: 22
gatcgaattc tcgcttacga tcatcaaaga gatcatacc                            39

<210> SEQ ID NO 23
<211> LENGTH: 38
<212> TYPE: DNA
<213> ORGANISM: Artificial Sequence
<220> FEATURE:
<223> OTHER INFORMATION: Synthetic Construct

<400> SEQUENCE: 23
gatcggatcc agcaagggcc accatatcac ataccgcc                             38

<210> SEQ ID NO 24
<211> LENGTH: 38
<212> TYPE: DNA
<213> ORGANISM: Artificial Sequence
<220> FEATURE:
<223> OTHER INFORMATION: Synthetic Construct

<400> SEQUENCE: 24
caggggaatt caccatgcga aattttttta acaaatgc                             38

<210> SEQ ID NO 25
<211> LENGTH: 23
<212> TYPE: DNA
<213> ORGANISM: Artificial Sequence
<220> FEATURE:
<223> OTHER INFORMATION: Synthetic Construct

<400> SEQUENCE: 25
gaacatatat ctcagggggac cac                                          23

<210> SEQ ID NO 26
<211> LENGTH: 47
<212> TYPE: DNA
<213> ORGANISM: Artificial Sequence
<220> FEATURE:
<223> OTHER INFORMATION: Synthetic Construct

<400> SEQUENCE: 26
gtggtcccct gagatatatg ttctaatgga gtacctattg cagagcg                 47

<210> SEQ ID NO 27
<211> LENGTH: 29
<212> TYPE: DNA
<213> ORGANISM: Artificial Sequence
<220> FEATURE:
<223> OTHER INFORMATION: Synthetic Construct

<400> SEQUENCE: 27
ttacggtttg ttactgtgac agctgaagc                                     29

<210> SEQ ID NO 28
<211> LENGTH: 53
<212> TYPE: DNA
<213> ORGANISM: Artificial Sequence
<220> FEATURE:
<223> OTHER INFORMATION: Synthetic Construct

<400> SEQUENCE: 28
gcttcagctg tcacagtaac aaaccgtaaa actgctctgg atgcatctct ggt          53

<210> SEQ ID NO 29
<211> LENGTH: 22
<212> TYPE: DNA
<213> ORGANISM: Artificial Sequence
<220> FEATURE:
<223> OTHER INFORMATION: Synthetic Construct

<400> SEQUENCE: 29
cagataaatc gccattcgtt ga                                            22

<210> SEQ ID NO 30
<211> LENGTH: 43
<212> TYPE: DNA
<213> ORGANISM: Artificial Sequence
<220> FEATURE:
<223> OTHER INFORMATION: Synthetic Construct

<400> SEQUENCE: 30
tcaacgaatg gcgatttatc tgcattccgg aacgttccag cgc                     43

<210> SEQ ID NO 31
<211> LENGTH: 50
<212> TYPE: DNA
<213> ORGANISM: Artificial Sequence
<220> FEATURE:
<223> OTHER INFORMATION: Synthetic Construct

<400> SEQUENCE: 31
ggtacgtctt tactgatgat taaccacacc ccaccgggca gttattttgc        50

<210> SEQ ID NO 32
<211> LENGTH: 50
<212> TYPE: DNA
<213> ORGANISM: Artificial Sequence
<220> FEATURE:
<223> OTHER INFORMATION: Synthetic Construct

<400> SEQUENCE: 32
gcaaaataac tgcccggtgg ggtgtggtta atcatcagta aagacgtacc        50

<210> SEQ ID NO 33
<211> LENGTH: 26
<212> TYPE: DNA
<213> ORGANISM: Artificial Sequence
<220> FEATURE:
<223> OTHER INFORMATION: Synthetic Construct

<400> SEQUENCE: 33
tatgtgacag gatttgttaa caggac                                  26

<210> SEQ ID NO 34
<211> LENGTH: 60
<212> TYPE: DNA
<213> ORGANISM: Artificial Sequence
<220> FEATURE:
<223> OTHER INFORMATION: Synthetic Construct

<400> SEQUENCE: 34
gtcctgttaa caaatcctgt cacatataaa ttattttgct caataatcag acgaagatgg   60

<210> SEQ ID NO 35
<211> LENGTH: 39
<212> TYPE: DNA
<213> ORGANISM: Artificial Sequence
<220> FEATURE:
<223> OTHER INFORMATION: Synthetic Construct

<400> SEQUENCE: 35
aggaggacag ctatgaaaat aattattttt agagtgcta                    39

<210> SEQ ID NO 36
<211> LENGTH: 36
<212> TYPE: DNA
<213> ORGANISM: Artificial Sequence
<220> FEATURE:
<223> OTHER INFORMATION: Synthetic Construct

<400> SEQUENCE: 36
gatcggatcc taaggaggac agctatgaaa ataatt                       36

<210> SEQ ID NO 37
<211> LENGTH: 34
<212> TYPE: DNA
<213> ORGANISM: Artificial Sequence
<220> FEATURE:
<223> OTHER INFORMATION: Synthetic Construct

<400> SEQUENCE: 37
ggtggtggtg acgaaaaata acttcgctga atcc                         34

<210> SEQ ID NO 38
<211> LENGTH: 32

```
<212> TYPE: DNA
<213> ORGANISM: Artificial Sequence
<220> FEATURE:
<223> OTHER INFORMATION: Synthetic Construct

<400> SEQUENCE: 38
cagtggtggt ggtggtggtg acgaaaaata ac                              32

<210> SEQ ID NO 39
<211> LENGTH: 31
<212> TYPE: DNA
<213> ORGANISM: Artificial Sequence
<220> FEATURE:
<223> OTHER INFORMATION: Synthetic Construct

<400> SEQUENCE: 39
gatcgaattc tcagtggtgg tggtggtggt g                               31

<210> SEQ ID NO 40
<211> LENGTH: 45
<212> TYPE: DNA
<213> ORGANISM: Artificial Sequence
<220> FEATURE:
<223> OTHER INFORMATION: Synthetic Construct

<400> SEQUENCE: 40
aaccacaccc caccgggcag ttattttgca gttgatgtca gaggg                45

<210> SEQ ID NO 41
<211> LENGTH: 45
<212> TYPE: DNA
<213> ORGANISM: Artificial Sequence
<220> FEATURE:
<223> OTHER INFORMATION: Synthetic Construct

<400> SEQUENCE: 41
ataactgccc ggtggggtgt ggttaatcat cagtaaagac gtacc                45

<210> SEQ ID NO 42
<211> LENGTH: 44
<212> TYPE: DNA
<213> ORGANISM: Artificial Sequence
<220> FEATURE:
<223> OTHER INFORMATION: Synthetic Construct

<400> SEQUENCE: 42
acacatatat cagtgccagg tacaacagcg gttacattgt ctgg                 44

<210> SEQ ID NO 43
<211> LENGTH: 46
<212> TYPE: DNA
<213> ORGANISM: Artificial Sequence
<220> FEATURE:
<223> OTHER INFORMATION: Synthetic Construct

<400> SEQUENCE: 43
acctggcact gatatatgtg taaaatcagc aaagcgataa aaaaca               46

<210> SEQ ID NO 44
<211> LENGTH: 47
<212> TYPE: DNA
<213> ORGANISM: Artificial Sequence
<220> FEATURE:
<223> OTHER INFORMATION: Synthetic Construct

<400> SEQUENCE: 44
```
gtgaatgaag agagtcaacc agaatgtccg gcagatggaa gagtccg         47

<210> SEQ ID NO 45
<211> LENGTH: 24
<212> TYPE: DNA
<213> ORGANISM: Artificial Sequence
<220> FEATURE:
<223> OTHER INFORMATION: Synthetic Construct

<400> SEQUENCE: 45
ttctggttga ctctcttcat tcac         24

<210> SEQ ID NO 46
<211> LENGTH: 46
<212> TYPE: DNA
<213> ORGANISM: Artificial Sequence
<220> FEATURE:
<223> OTHER INFORMATION: Synthetic Construct

<400> SEQUENCE: 46
ggcattaata ctgaattgtc atcatcaggg ggcgcgttct gttcgc         46

<210> SEQ ID NO 47
<211> LENGTH: 25
<212> TYPE: DNA
<213> ORGANISM: Artificial Sequence
<220> FEATURE:
<223> OTHER INFORMATION: Synthetic Construct

<400> SEQUENCE: 47
atgatgacaa ttcagtatta atgcc         25

<210> SEQ ID NO 48
<211> LENGTH: 38
<212> TYPE: DNA
<213> ORGANISM: Artificial Sequence
<220> FEATURE:
<223> OTHER INFORMATION: Synthetic Construct

<400> SEQUENCE: 48
aggaggacag ctatgaagtg tatattattt aaatgggt         38

<210> SEQ ID NO 49
<211> LENGTH: 34
<212> TYPE: DNA
<213> ORGANISM: Artificial Sequence
<220> FEATURE:
<223> OTHER INFORMATION: Synthetic Construct

<400> SEQUENCE: 49
gatcggatcc taaggaggac agctatgaag tgta         34

<210> SEQ ID NO 50
<211> LENGTH: 31
<212> TYPE: DNA
<213> ORGANISM: Artificial Sequence
<220> FEATURE:
<223> OTHER INFORMATION: Synthetic Construct

<400> SEQUENCE: 50
ggtggtggtg gtcattatta aactgcactt c         31

<210> SEQ ID NO 51
<211> LENGTH: 32
<212> TYPE: DNA
<213> ORGANISM: Artificial Sequence

```
<220> FEATURE:
<223> OTHER INFORMATION: Synthetic Construct

<400> SEQUENCE: 51
cagtggtggt ggtggtggtg gtcattatta aa                                32

<210> SEQ ID NO 52
<211> LENGTH: 32
<212> TYPE: DNA
<213> ORGANISM: Artificial Sequence
<220> FEATURE:
<223> OTHER INFORMATION: Synthetic Construct

<400> SEQUENCE: 52
gatcggatcc ctggtatcgt attacttcag cc                                32

<210> SEQ ID NO 53
<211> LENGTH: 30
<212> TYPE: DNA
<213> ORGANISM: Artificial Sequence
<220> FEATURE:
<223> OTHER INFORMATION: Synthetic Construct

<400> SEQUENCE: 53
gatcgaattc ctgcacacta cgaaaccagc                                   30

<210> SEQ ID NO 54
<211> LENGTH: 26
<212> TYPE: DNA
<213> ORGANISM: Artificial Sequence
<220> FEATURE:
<223> OTHER INFORMATION: Synthetic Construct

<400> SEQUENCE: 54
tcagtgacag gatttgttaa caggac                                       26

<210> SEQ ID NO 55
<211> LENGTH: 53
<212> TYPE: DNA
<213> ORGANISM: Artificial Sequence
<220> FEATURE:
<223> OTHER INFORMATION: Synthetic Construct

<400> SEQUENCE: 55
gtcctgttaa caaatcctgt cactgataaa ttatttcgtt caacaataag ccg         53
```